United States Patent
Gifford et al.

(10) Patent No.: US 12,059,144 B2
(45) Date of Patent: Aug. 13, 2024

(54) GUIDANCE SYSTEM MOUNTS FOR SURGICAL INTRODUCERS

(71) Applicant: Vycor Medical, Inc., Boca Raton, FL (US)

(72) Inventors: Aaron James Gifford, Lake Elsinore, CA (US); Clark Berg Foster, Mission Viejo, CA (US); Donald Clevenger, Huntington Beach, CA (US)

(73) Assignee: Vycor Medical, Inc., Boca Raton, FL (US)

( * ) Notice: Subject to any disclaimer, the term of this patent is extended or adjusted under 35 U.S.C. 154(b) by 405 days.

(21) Appl. No.: 17/471,872

(22) Filed: Sep. 10, 2021

(65) Prior Publication Data

US 2021/0401422 A1    Dec. 30, 2021

Related U.S. Application Data

(63) Continuation of application No. 16/369,848, filed on Mar. 29, 2019, now Pat. No. 11,116,487, which is a
(Continued)

(51) Int. Cl.
*A61B 17/02* (2006.01)
*A61B 17/34* (2006.01)
(Continued)

(52) U.S. Cl.
CPC .......... *A61B 17/02* (2013.01); *A61B 17/3415* (2013.01); *A61B 17/3421* (2013.01);
(Continued)

(58) Field of Classification Search
CPC ................ A61B 17/02; A61B 17/3421; A61B 2017/347; A61B 1/32; A61B 34/20
See application file for complete search history.

(56) References Cited

U.S. PATENT DOCUMENTS

| 1,849,701 A | 3/1932 | Allyn |
| 2,769,441 A | 11/1956 | Abramson |

(Continued)

FOREIGN PATENT DOCUMENTS

| CN | 101720207 A | 6/2010 |
| CN | 201879787 U | 6/2011 |

(Continued)

OTHER PUBLICATIONS

Alberti et al., "Frameless Navigation and Endoscopy", J. Neurosurg., Sep. 2001;95(3), pp. 541-543.

(Continued)

*Primary Examiner* — Eduardo C Robert
*Assistant Examiner* — Michelle C Eckman
(74) *Attorney, Agent, or Firm* — Culhane Haughian & Walsh PLLC; Michael P. F. Phelps

(57) ABSTRACT

A delicate tissue retraction system for use with a navigation probe having a probe shaft and a probe tip at a distal end of the probe shaft. The delicate tissue retraction system includes a retractor and an introducer that is removably installed within the retractor. The introducer has a wall forming a hollow channel extending from a proximal introducer end to a distal introducer end. A mount is integrally formed with the introducer and extends from the distal introducer end into the channel. The mount is positioned to surround the probe tip when the navigation probe is at a fully inserted position within the introducer with the probe tip at the distal introducer end.

18 Claims, 9 Drawing Sheets

Related U.S. Application Data continuation of application No. 15/613,904, filed on Jun. 5, 2017, now Pat. No. 10,327,748, which is a continuation of application No. 14/711,305, filed on May 13, 2015, now Pat. No. 9,737,287.

(60) Provisional application No. 61/992,378, filed on May 13, 2014.

(51) Int. Cl.
*A61B 34/20* (2016.01)
*A61B 1/32* (2006.01)
*A61B 90/00* (2016.01)
*A61B 90/10* (2016.01)
*A61B 90/57* (2016.01)

(52) U.S. Cl.
CPC .......... *A61B 17/3439* (2013.01); *A61B 34/20* (2016.02); *A61B 1/32* (2013.01); *A61B 2017/3456* (2013.01); *A61B 17/3468* (2013.01); *A61B 2017/347* (2013.01); *A61B 2034/2051* (2016.02); *A61B 2034/2068* (2016.02); *A61B 2090/062* (2016.02); *A61B 2090/0811* (2016.02); *A61B 90/10* (2016.02); *A61B 2090/103* (2016.02); *A61B 2090/376* (2016.02); *A61B 90/57* (2016.02)

(56) References Cited

U.S. PATENT DOCUMENTS

| | | | |
|---|---|---|---|
| 2,922,415 A | 1/1960 | Campagna |
| 3,417,746 A | 12/1968 | Moore |
| 3,608,547 A | 9/1971 | Sato |
| 3,626,471 A | 12/1971 | Florin |
| 3,690,323 A | 9/1972 | Wortman et al. |
| 3,766,910 A | 10/1973 | Lake |
| 3,789,829 A | 2/1974 | Hasson |
| 3,882,855 A | 5/1975 | Schulte et al. |
| 3,888,117 A | 6/1975 | Lewis |
| 4,263,900 A | 4/1981 | Nicholson |
| 4,312,353 A | 1/1982 | Shahbabian |
| 4,386,602 A | 6/1983 | Sheldon et al. |
| 4,502,468 A | 3/1985 | Burgin |
| 4,585,438 A | 4/1986 | Makler |
| 4,636,199 A | 1/1987 | Victor |
| 4,638,798 A | 1/1987 | Sheldon et al. |
| 4,742,815 A | 5/1988 | Ninan et al. |
| 4,931,039 A | 6/1990 | Coe et al. |
| 4,945,896 A | 8/1990 | Gade |
| 5,052,373 A | 10/1991 | Michelson |
| 5,135,526 A | 8/1992 | Zinnanti et al. |
| 5,160,323 A | 11/1992 | Andrew |
| 5,183,464 A | 2/1993 | Dubrul et al. |
| 5,230,623 A | 7/1993 | Guthrie et al. |
| 5,249,568 A | 10/1993 | Brefka et al. |
| 5,251,127 A | 10/1993 | Raab |
| 5,256,149 A | 10/1993 | Banik et al. |
| 5,271,380 A | 12/1993 | Riek et al. |
| 5,275,583 A | 1/1994 | Crainich |
| 5,284,130 A | 2/1994 | Ratliff |
| 5,305,203 A | 4/1994 | Raab |
| 5,320,611 A | 6/1994 | Bonutti et al. |
| 5,334,150 A | 8/1994 | Kaali |
| 5,356,421 A | 10/1994 | Castro |
| 5,376,076 A | 12/1994 | Kaali |
| 5,380,291 A | 1/1995 | Kaali |
| 5,409,453 A | 4/1995 | Lundquist et al. |
| 5,431,151 A | 7/1995 | Riek et al. |
| 5,431,676 A | 7/1995 | Dubrul et al. |
| 5,441,041 A | 8/1995 | Sauer et al. |
| 5,445,142 A | 8/1995 | Hassler |
| 5,467,762 A | 11/1995 | Sauer et al. |
| 5,513,238 A | 4/1996 | Leber et al. |
| 5,540,711 A | 7/1996 | Kieturakis et al. |
| 5,551,947 A | 9/1996 | Kaali |
| 5,555,283 A | 9/1996 | Shui et al. |
| 5,562,696 A | 10/1996 | Nobles et al. |
| 5,569,160 A | 10/1996 | Sauer et al. |
| D377,093 S | 12/1996 | Michelson |
| 5,591,192 A | 1/1997 | Privitera et al. |
| 5,609,562 A | 3/1997 | Kaali |
| 5,658,236 A | 8/1997 | Sauer et al. |
| 5,662,111 A | 9/1997 | Cosman |
| 5,665,072 A | 9/1997 | Yoon |
| 5,676,673 A | 10/1997 | Ferre et al. |
| 5,685,820 A | 11/1997 | Riek et al. |
| 5,702,761 A | 12/1997 | DiChiara et al. |
| 5,738,628 A | 4/1998 | Sierocuk et al. |
| 5,748,703 A | 5/1998 | Cosman |
| 5,748,767 A | 5/1998 | Raab |
| 5,762,629 A | 6/1998 | Kambin |
| 5,778,043 A | 7/1998 | Cosman |
| 5,782,807 A | 7/1998 | Falvai et al. |
| 5,785,648 A | 7/1998 | Min |
| 5,792,044 A | 8/1998 | Foley et al. |
| 5,800,352 A | 9/1998 | Ferre et al. |
| 5,803,089 A | 9/1998 | Ferre et al. |
| 5,829,444 A | 11/1998 | Ferre et al. |
| 5,846,249 A | 12/1998 | Thompson |
| 5,848,967 A | 12/1998 | Cosman |
| 5,860,996 A | 1/1999 | Urban et al. |
| 5,873,822 A | 2/1999 | Ferre et al. |
| 5,891,157 A | 4/1999 | Day et al. |
| 5,902,272 A | 5/1999 | Eggers et al. |
| 5,921,992 A | 7/1999 | Costales et al. |
| 5,947,981 A | 9/1999 | Cosman |
| 5,967,970 A | 10/1999 | Cowan et al. |
| 5,967,980 A | 10/1999 | Ferre et al. |
| 5,971,997 A | 10/1999 | Guthrie et al. |
| 6,005,919 A | 12/1999 | Kooy et al. |
| 6,006,126 A | 12/1999 | Cosman |
| 6,007,481 A | 12/1999 | Riek et al. |
| 6,041,101 A | 3/2000 | Kooy et al. |
| 6,047,218 A | 4/2000 | Whayne et al. |
| 6,083,191 A | 7/2000 | Rose et al. |
| 6,093,145 A | 7/2000 | Berg et al. |
| 6,096,038 A | 8/2000 | Michelson |
| 6,120,465 A | 9/2000 | Guthrie et al. |
| 6,129,685 A | 10/2000 | Howard |
| 6,142,931 A | 11/2000 | Kaji et al. |
| 6,156,054 A | 12/2000 | Zadno-Azizi et al. |
| 6,159,178 A | 12/2000 | Sharkawy et al. |
| 6,167,295 A | 12/2000 | Cosman |
| 6,175,756 B1 | 1/2001 | Ferre et al. |
| 6,179,826 B1 | 1/2001 | Aebischer et al. |
| 6,214,017 B1 | 4/2001 | Stoddard et al. |
| 6,221,078 B1 | 4/2001 | Bylsma |
| 6,224,599 B1 | 5/2001 | Bayham et al. |
| 6,228,059 B1 | 5/2001 | Astarita |
| 6,236,875 B1 | 5/2001 | Bucholz et al. |
| 6,245,052 B1 | 6/2001 | Orth et al. |
| 6,256,859 B1 | 7/2001 | Stoddard et al. |
| 6,259,943 B1 | 7/2001 | Cosman et al. |
| 6,275,725 B1 | 8/2001 | Cosman |
| 6,277,069 B1 | 8/2001 | Gray |
| 6,278,766 B1 | 8/2001 | Kooy et al. |
| 6,283,912 B1 | 9/2001 | Hu et al. |
| 6,293,952 B1 | 9/2001 | Brosens et al. |
| 6,296,647 B1 | 10/2001 | Robionek et al. |
| 6,312,443 B1 | 11/2001 | Stone |
| 6,326,875 B1 | 12/2001 | Tuovinen |
| 6,331,180 B1 | 12/2001 | Cosman et al. |
| 6,341,231 B1 | 1/2002 | Ferre et al. |
| 6,351,659 B1 | 2/2002 | Vilsmeier |
| 6,351,661 B1 | 2/2002 | Cosman |
| 6,359,959 B1 | 3/2002 | Butler et al. |
| 6,364,832 B1 | 4/2002 | Propp |
| 6,371,964 B1 | 4/2002 | Vargas et al. |
| 6,374,135 B1 | 4/2002 | Bucholz |
| 6,383,191 B1 | 5/2002 | Zdeblick et al. |
| 6,405,072 B1 | 6/2002 | Cosman |
| 6,409,686 B1 | 6/2002 | Guthrie et al. |

(56) References Cited

U.S. PATENT DOCUMENTS

| | | |
|---|---|---|
| 6,416,520 B1 | 7/2002 | Kynast et al. |
| 6,425,859 B1 | 7/2002 | Foley et al. |
| 6,445,944 B1 | 9/2002 | Ostrovsky |
| 6,459,769 B1 | 10/2002 | Cosman |
| 6,461,330 B1 | 10/2002 | Miyagi |
| 6,478,028 B1 | 11/2002 | Paolitto et al. |
| 6,478,806 B2 | 11/2002 | McFarlane |
| 6,551,240 B2 | 4/2003 | Henzler |
| 6,565,574 B2 | 5/2003 | Michelson |
| 6,589,211 B1 | 7/2003 | MacLeod |
| 6,595,917 B2 | 7/2003 | Nieto |
| 6,596,008 B1 | 7/2003 | Kambin |
| 6,599,292 B1 | 7/2003 | Ray |
| 6,602,227 B1 | 8/2003 | Cimino et al. |
| 6,605,036 B1 | 8/2003 | Wild |
| 6,613,038 B2 | 9/2003 | Bonutti et al. |
| 6,654,999 B2 | 12/2003 | Stoddard et al. |
| 6,662,036 B2 | 12/2003 | Cosman |
| 6,669,685 B1 | 12/2003 | Rizoiu et al. |
| 6,675,040 B1 | 1/2004 | Cosman |
| 6,685,630 B2 | 2/2004 | Sauer et al. |
| 6,761,687 B1 | 7/2004 | Doshi et al. |
| D495,053 S | 8/2004 | Laun |
| 6,863,674 B2 | 3/2005 | Kasahara et al. |
| 6,896,680 B2 | 5/2005 | Michelson |
| 6,942,634 B2 | 9/2005 | Odland |
| 7,081,089 B2 | 7/2006 | Bonadio et al. |
| 7,153,304 B2 | 12/2006 | Robie et al. |
| 7,235,084 B2 | 6/2007 | Skakoon et al. |
| 7,449,011 B2 | 11/2008 | Wenchell et al. |
| 7,474,820 B2 | 1/2009 | Vayser et al. |
| 7,479,150 B2 | 1/2009 | Rethy et al. |
| 7,510,524 B2 | 3/2009 | Vayser et al. |
| 7,686,492 B2 | 3/2010 | Vayser et al. |
| 7,799,035 B2 | 9/2010 | Krueger et al. |
| 8,360,970 B2 | 1/2013 | Mangiardi |
| 8,386,052 B2 | 2/2013 | Harris et al. |
| 8,409,083 B2 | 4/2013 | Mangiardi |
| 8,608,650 B2 | 12/2013 | Mangiardi |
| 8,608,769 B2 | 12/2013 | Kahle et al. |
| 8,679,088 B2 | 3/2014 | Abrahams |
| 9,216,015 B2 | 12/2015 | Wilson |
| 9,307,969 B2 | 4/2016 | Novak et al. |
| 10,258,316 B2 | 4/2019 | Rhad et al. |
| 10,327,748 B2 | 6/2019 | Gifford et al. |
| 2001/0010002 A1 | 7/2001 | Michelson |
| 2001/0027271 A1 | 10/2001 | Franck et al. |
| 2001/0037050 A1 | 11/2001 | Lemperle |
| 2002/0022764 A1 | 2/2002 | Smith et al. |
| 2002/0151769 A1 | 10/2002 | Kim |
| 2002/0161366 A1 | 10/2002 | Robie et al. |
| 2003/0040753 A1 | 2/2003 | Daum et al. |
| 2003/0073934 A1 | 4/2003 | Putz |
| 2003/0139648 A1 | 7/2003 | Foley et al. |
| 2003/0145865 A1 | 8/2003 | Sterman et al. |
| 2004/0024291 A1 | 2/2004 | Zinkel |
| 2004/0059375 A1 | 3/2004 | Ginn et al. |
| 2004/0068172 A1 | 4/2004 | Nowinski et al. |
| 2004/0097792 A1 | 5/2004 | Moll et al. |
| 2004/0102804 A1 | 5/2004 | Chin |
| 2004/0186346 A1 | 9/2004 | Smith et al. |
| 2004/0230100 A1 | 11/2004 | Shluzas |
| 2005/0273132 A1 | 12/2005 | Shluzas et al. |
| 2005/0277811 A1 | 12/2005 | Richards et al. |
| 2006/0041270 A1 | 2/2006 | Lenker et al. |
| 2006/0122462 A1 | 6/2006 | Roth et al. |
| 2006/0212062 A1 | 9/2006 | Farascioni |
| 2006/0287583 A1* | 12/2006 | Mangiardi ............... A61B 1/32 600/210 |
| 2007/0129747 A1 | 6/2007 | Dorman |
| 2007/0135679 A1 | 6/2007 | Hunt et al. |
| 2007/0232874 A1 | 10/2007 | Ince |
| 2008/0100061 A1 | 5/2008 | Sage et al. |
| 2008/0109026 A1* | 5/2008 | Kassam ............ A61B 17/00234 600/101 |
| 2008/0119693 A1 | 5/2008 | Makower et al. |
| 2009/0048622 A1* | 2/2009 | Wilson ............... A61B 17/3431 606/190 |
| 2009/0312611 A1* | 12/2009 | Mangiardi ......... A61B 17/3421 600/210 |
| 2010/0010315 A1 | 1/2010 | Mangiardi |
| 2011/0118710 A1 | 5/2011 | Begemann et al. |
| 2011/0160672 A1 | 6/2011 | Boebel et al. |
| 2011/0196205 A1 | 8/2011 | Hathaway et al. |
| 2011/0301424 A1 | 12/2011 | Steigerwald |
| 2012/0016204 A1 | 1/2012 | Bastia |
| 2012/0016316 A1 | 1/2012 | Zhuang et al. |
| 2012/0035424 A1 | 2/2012 | Schulte |
| 2012/0071748 A1* | 3/2012 | Mark ................. A61B 17/3417 600/249 |
| 2012/0253375 A1 | 10/2012 | Mark et al. |
| 2012/0265058 A1 | 10/2012 | Carrascosa |
| 2012/0289816 A1 | 11/2012 | Mark et al. |
| 2013/0066154 A1* | 3/2013 | Mangiardi ......... A61M 25/0102 600/202 |
| 2013/0102851 A1 | 4/2013 | Mark et al. |
| 2013/0102886 A1 | 4/2013 | Mark et al. |
| 2013/0204095 A1 | 8/2013 | Mark et al. |
| 2013/0204287 A1 | 8/2013 | Mark et al. |
| 2013/0211200 A1 | 8/2013 | Brannon |
| 2013/0245381 A1 | 9/2013 | Dang et al. |
| 2014/0107426 A1 | 4/2014 | Wilson |
| 2014/0171873 A1* | 6/2014 | Mark ................. A61B 17/3417 604/164.01 |
| 2014/0187922 A1 | 7/2014 | Mark et al. |
| 2016/0015374 A1 | 1/2016 | Gifford et al. |
| 2016/0317182 A1 | 11/2016 | Mark et al. |
| 2017/0000579 A1 | 1/2017 | Mark et al. |
| 2017/0265893 A1 | 9/2017 | Mark et al. |
| 2017/0265894 A1 | 9/2017 | Mark et al. |
| 2017/0360291 A1 | 12/2017 | Chegini et al. |
| 2018/0014890 A1 | 1/2018 | Stanton et al. |
| 2018/0085182 A1 | 3/2018 | Ewers et al. |
| 2018/0125603 A1 | 5/2018 | Cantor et al. |
| 2018/0161024 A1 | 6/2018 | Davis et al. |
| 2021/0085363 A1 | 3/2021 | Mark et al. |
| 2021/0236161 A1 | 8/2021 | Mark et al. |

FOREIGN PATENT DOCUMENTS

| | | |
|---|---|---|
| CN | 103619264 A | 3/2014 |
| CN | 203724147 U | 7/2014 |
| DE | 102005032197 A1 | 1/2007 |
| JP | 02289221 A | 11/1990 |
| JP | 05344978 | 12/1993 |
| JP | 09224943 | 9/1997 |
| JP | 2000287915 A | 10/2000 |
| JP | 2003153907 | 5/2003 |
| RU | 45928 U1 | 6/2005 |
| RU | 55570 U1 | 8/2006 |
| SU | 131027 A1 | 3/1959 |
| SU | 349136 | 9/1972 |
| SU | 685840 A1 | 12/1977 |
| SU | 1521465 A1 | 11/1989 |
| WO | 0143627 A1 | 6/2001 |
| WO | 2006017507 A2 | 2/2006 |
| WO | 2006050047 A2 | 5/2006 |
| WO | 2006050225 A2 | 5/2006 |
| WO | 2013063027 A1 | 5/2013 |
| WO | 2014137530 A1 | 9/2014 |
| WO | 2014137551 A1 | 9/2014 |

OTHER PUBLICATIONS

Alexander et al., "Chapter 20: Stereotactic Frame Systems: The COMPASS System", Advanced Neurosurgical Navigation, 1999, pp. 267-277.

Amstutz et al., "A-Mode Ultrasound-Based Registration in Computer-Aided Surgery of the Skull", Arch. Otolaryngol Head Neck Surg., 2003, 129(12), pp. 1310-1316.

(56) References Cited

OTHER PUBLICATIONS

Andrew et al., "A Review of Brain Retraction and Recommendations for Minimizing Intraoperative Brain Injury", Neurosurgery, 1993, 33(6), pp. 1052-1063.
Burtscher et al., "Neuroendoscopy Based on Computer Assisted Adjustment of the Endoscope Holder in the Laboratory", Minimum Invasive Neurosurgery, 2003, 46, pp. 208-214.
Chinese Office Action for Chinese Application No. 201580031654.3, dated Sep. 30, 2017, 18 pages.
Decision for Rejection for Japanese Application No. 2009-539227, dated May 31, 2013, 8 pages.
Del Ray Medical Center Press Release, "Advanced Neuroscience Network Brings New Innovations in Neurosurgery to South Florida", May 13, 2015, pp. 1-6.
Ding et al., "Endoport-assisted Microsurgical Resection of Cerebral Cavernous Malformations", J. Clin. Neurosci., Jun. 2015, vol. 22, No. 6, pp. 1025-1029. (Abstract only).
Eldeib et al., "Rigid Neuroendoscope Navigation System for Minimally Invasive Surgery", Engineering in Medicine and Biology, 1999, 1 page. (Abstract only).
Engh et al., "NeuroendoportSM Surgery Facilitates Removal of Hard-to-Reach Brain Tumors", Neurosurgery News, Spring 2009, vol. 10, No. 2, 8 pages.
European Communication for European Application No. 15 793 215.3, dated Jan. 15, 2018, 4 pages.
European Communication for European Application No. 17 868 180.5, dated Jun. 17, 2020, 1 page.
Extended European Communication for European Application No. 06 840 022.5, dated Mar. 26, 2013, 7 pages.
Extended European Communication for European Application No. 15 793 215.3, dated Mar. 24, 2017—6 pages.
Extended European Communication for European Application No. 17 868 180.5, dated May 29, 2020, 5 pages.
Final Office Action for U.S. Appl. No. 14/134,360, dated Jan. 12, 2016, 13 pages.
Final Office Action for U.S. Appl. No. 14/727,374, dated Nov. 23, 2016, 14 pages.
Final Office Action for U.S. Appl. No. 15/372,890, dated Feb. 21, 2019, 15 pages.
Final Office Action for U.S. Appl. No. 15/372,890, dated Oct. 1, 2018, 31 pages.
Fukamachi et al., "Postoperative Intracerebral Hemorrhages: A Survey of Computed Tomographic Findings After 1074 Intracranial Operations", Surg. Neurol., Jun. 1985, 23(6), pp. 575-580.
Greenfield et al., "Stereotactic Minimally Invasive Tubular Retractors System for Deep Brain Lesions", Neurosurgery, 2008, 63(4), pp. 334-339. (Abstract only).
Gumprecht et al., "Neuroendoscopy Combined with Frameless Neuronavigation", British Journal of Neurosurgery, 2000, 14(2), pp. 129-131.
Hellwig et al., "Neuroendoscopic Treatment for Colloid Cysts of the Third Ventricle: The Experience of a Decade", Neurosurgery, Mar. 2003, vol. 52, Iss. 3, pp. 525-533.
Herrera et al., "Use of Transparent Plastic Tubular Retractor in Surgery for Deep Brain Lesions: A Case Series", Surgical Technology International XIX, published in 2010, pp. 1-4.
Hilton et al., "METRx Microdiscectomy Surgical Technique", Medtronic Sofamor Danek, 2001, 20 pages.
International Preliminary Report on Patentability for International Application No. PCT/US2006/061246, dated Jun. 3, 2009, 5 pages.
International Preliminary Report on Patentability for International Application No. PCT/US2015/030528, dated Nov. 15, 2016, 7 pages.
International Preliminary Report on Patentability for International Application No. PCT/US2017/060373, dated May 7, 2019, 8 pages.
International Search Report and Written Opinion for International Application PCT/US2006/061246, dated Sep. 11, 2007, 5 pages.
International Search Report and Written Opinion for International Application PCT/US2015/030528, dated Aug. 14, 2020, 8 pages.
International Search Report and Written Opinion for International Application PCT/US2017/060373, dated Jan. 23, 2018, 8 pages.
K043602 510(k) Summary, Feb. 23, 2005, 5 pages.
K060973 510(k) Summary, Jul. 26, 2006, 6 pages.
Kelly et al., "The Stereotaxic Retractor in Computer-Assisted Stereotaxic Microsurgery", J. Neurosurgery, 1988, 69, pp. 301-306.
Konen et al., "An Image-based Navigation Support System for Neuroendoscopic Surgery", in: R. Ahlers (ed.), 5. Symposium Bildverarbeitung, 1997, Technische Akademie Esslingen, 8 pages.
Kubo et al., "A Newly Designed Disposable Introducer Sheath for a Ventricular Fiberscope", Minim Invasive Neurosurg, 2004, 47(2), pp. 124-126.
Lemole et al., "Cranial Application of Frameless Stereotaxy", Barrow Neurological Institute, Barrow Quarterly, 2001, vol. 17, No. 1, 12 pages.
McInerney et al., "Frameless Stereotaxy of the Brain", The Mount Sinai Journal of Medicine, Sep. 2000, vol. 67, No. 4, pp. 300-310.
Mettler et al., "Optical Trocar Systems: Laparoscopic Entry and its Complications (A Study of Cases in Germany)", Gynaecological Endoscopy, Dec. 1999, vol. 8, Iss. 6, pp. 383-389. (Abstract only).
Nagatani et al., "High Definition Exoscope System for Microneurosurgery: Use of an Exoscope in Combination with Tubular Retraction and Frameless Neuronavigation for Microsurgical Resection of Deep Brain Lesions", No Shinkei Geka, Jul. 2015, 43(7), pp. 611-617.
"Neuronavigation", from Wikipedia, dated Jul. 30, 2014, 2 pages.
NICO Corporation Press Release, "NICO Corporation Gains Market Expansion after Multiple Published Clinical Articles Support Access Technology for Deep Brain Lesions", May 5, 2015, 2 pages.
Non Final Office Action for U.S. Appl. No. 14/727,374, dated Jul. 22, 2016, 35 pages.
Non Final Office Action for U.S. Appl. No. 14/711,305, dated Dec. 7, 2016, 42 pages.
Non Final Office Action for U.S. Appl. No. 14/727,361, dated Jul. 14, 2016, 31 pages.
Non Final Office Action for U.S. Appl. No. 15/004,332, dated Feb. 14, 2017, 13 pages.
Non Final Office Action for U.S. Appl. No. 15/004,332, dated Nov. 18, 2016, 26 pages.
Non Final Office Action for U.S. Appl. No. 15/372,890, dated Oct. 1, 2018, 31 pages.
Non Final Office Action for U.S. Appl. No. 15/613,904, dated Oct. 5, 2018, 34 pages.
Non Final Office Action for U.S. Appl. No. 16/369,862, dated Oct. 13, 2020, 27 pages.
Notice of Allowance for U.S. Appl. No. 13/674,507, mailed Dec. 9, 2015, 7 pages.
Notice of Allowance for U.S. Appl. No. 14/134,360, mailed Mar. 11, 2016, 10 pages.
Notice of Allowance for U.S. Appl. No. 14/711,305, mailed Apr. 18, 2017, 11 pages.
Notice of Allowance for U.S. Appl. No. 14/727,361, mailed Sep. 21, 2016, 8 pages.
Notice of Allowance for U.S. Appl. No. 14/727,374, mailed Jan. 19, 2017, 9 pages.
Notice of Allowance for U.S. Appl. No. 15/004,332, mailed Jun. 14, 2017, 7 pages.
Notice of Allowance for U.S. Appl. No. 15/083,916, mailed Jan. 30, 2018, 12 pages.
Notice of Allowance for U.S. Appl. No. 15/083,940, mailed Jan. 22, 2018, 7 pages.
Notice of Allowance for U.S. Appl. No. 15/372,890, mailed Mar. 26, 2019, 8 pages.
Notice of Allowance for U.S. Appl. No. 15/613,904, mailed Feb. 8, 2019, 9 pages.
Notice of Allowance for U.S. Appl. No. 15/805,821, mailed Sep. 25, 2019, 9 pages.
Office Action for U.S. Appl. No. 13/674,507, dated Jul. 27, 2015, 11 pages.
Office Action for U.S. Appl. No. 14/134,360, dated Jul. 7, 2015, 23 pages.

(56) References Cited

OTHER PUBLICATIONS

Ogura et al., "New Microsurgical Technique for Intraparenchymal Lesions of the Brain: Transcyclinder Approach", Aeta Neurochirurgica (Wein) 2006, 148, pp. 779-785.
O'Shaughnessy, P., "New Brain Tumor Technology Helps Man Who Took Two Bullets to the Head Return to Normal Life", Daily News, Jun. 19, 2011, 2 pages.
Otsuki et al., "Stereotactic Guiding Tube for Open-System Endoscopy: A New Approach for the Stereotactic Endoscopic Resection of Intra-Axial Brain Tumors", Neurosurgery, 1990, 27(2), pp. 326-330.
Preliminary Amendment and Request for Interference for U.S. Appl. No. 14/134,360, dated Dec. 23, 2013, 8 pages.
Prevedello et al., "Vycor ViewSite TC®: Endoscope Guided Intraparenchinal Brain Tumor Ressection", Ohio State University Medical Center Minimally Invasive Neurosurgery, 2 pages.
Rampini et al., "Stereotactically Guided Endoscopy for the Treatment of Arachnoid Cysts", Pediatric Neurosurgery, 1998, 29(2), pp. 102-104. (Abstract only).
Raza et al., "Minimally Evasive Trans-Portal Resection of Deep Intracranial Lesions", Neurosurgery, vol. 54, Feb. 2011, pp. 1-7.
Recinos et al., Use of Minimally Invasive Tubular Retraction System for Deep-seated Tumors in Pediatric Patients, J. Neurosurg. Pediatrics 7, 2011, pp. 516-521.
Ross et al., "A Simple Stereotactic Retractor for the use with the Leskell Stereotactic System", Neurosurgery, 1993, 32(3), pp. 475-476, discussion p. 476.
Rymarczuk et al., "Use of Minimally Invasive Retractor System for Retrieval of Intracranial Fragments in Wartime Trauma", World Neurosurgery, 2015, pp. 1-26.
Scholz et al., "Development of an Endoscopic Navigation System Based on Digital Image Processing", Computer Aided Surgery, 1998, 3(3), pp. 134-143. (Abstract only).
Scholz et al., "Virtual Image Navigation: A New Method to Control Intraoperative Bleeding in Neuroendoscopic Surgery", Neurosurg. Focus, 2000, 8(6), pp. 1-8.
Shoakazemi et al., "A 3D Endoscopic Transtubular Transcallosal Approach to the Third Ventrile", J. Neurosurg., 2015, pp. 1-10.
Shults et al., Neuro-opthalmic Complications of Intracranial Catheters, Neurosurgery, vol. 33, No. 1, Jul. 1993, pp. 135-138.
Slavin, K. "Testimonials", no date, but admitted as prior art between Jun. 17, 2005 and Mar. 27, 2012, 4 pages.
Spetzger et al., "Navigational Microneurosurgery: Experience with EasyGuide Neuro", Medicamundi, 1997, 41(1), pp. 28-35.
Tao et al., "Microsurgical Resection for Lateral Ventricular Meningiomas with Neuronavigation and Tubular Retractor System", Chin. J. Neurosurgery, vol. 31, No. 4, 2015, pp. 332-336. (Abstract only).
UPMC: Minimally Invasive Brain Surgery, Legacy of Innovations, Breakthroughs in Minimally Invasive Brain Surgery at UPMC, 2014, 1 page.
Vycor Medical, "Vycor ViewSite TC: Endoscopic Intraparenchimal Brain Tumor Resection with Image Guidance," 2 pages, no date but admitted as prior art between Jun. 17, 2005 and Mar. 27, 2012, 2 pages.
Wang et al., "Endoscopic Hematoma Evacuation in Patients with Spontaneous Supratentorial Intracerebral Hemorrhage", Journal of the Chinese Medical Association, 78, 2015, pp. 101-107.
Zhong et al., "Brain Retraction Injury", Neurological Research, Dec. 2003, vol. 25, pp. 831-838.
Entire patent prosecution history of U.S. Appl. No. 11/155,175 filed Jun. 17, 2005, entitled, "Surgical Access Instruments for Use With Delicate Tissues."
Entire patent prosecution history of U.S. Appl. No. 11/665,667, filed Apr. 18, 2007, entitled, "Apparatus and Methods for Performing Brain Surgery."
Entire patent prosecution history of U.S. Appl. No. 12/545,686, filed Aug. 29, 2009, entitled, "Surgical Access Instruments for Use With Delicate Tissues."
Entire patent prosecution history of U.S. Appl. No. 12/545,719, filed Aug. 21, 2009, and entitled, "Surgical Access Methods for Use With Delicate Tissues."
Entire patent prosecution history of U.S. Appl. No. 13/431,280, filed Mar. 27, 2012, entitled, "Tissue Retractor Apparatus and Methods."
Entire patent prosecution history of U.S. Appl. No. 13/674,507, filed Nov. 12, 2012, entitled, "Tissue Retractor Apparatus and Methods."
Entire patent prosecution history of U.S. Appl. No. 14/134,360, filed Dec. 9, 2013, entitled, "Apparatus and Methods for Performing Brain Surgery."
Entire patent prosecution history of U.S. Appl. No. 14/711,305, filed May 13, 2015, entitled, "Guidance System Mounts for Surgical Introducers."
Entire patent prosecution history of U.S. Appl. No. 15/613,904, filed Jun. 5, 2017, entitled, "Guidance System Mounts for Surgical Introducers."
Entire patent prosecution history of U.S. Appl. No. 16/369,848, filed Mar. 29, 2019, entitled, "Guidance System Mounts for Surgical Introducers."
Canadian Examination Report for Canadian Application No. 3,043,182, dated Sep. 12, 2022, 9 pages.
Chinese Office Action for Chinese Application No. 201780082607.0, dated Dec. 27, 2021, with translation, 19 pages.
Non Final Office Action for U.S. Appl. No. 17/479,325, mailed Aug. 29, 2023, 16 pages.
Japanese Notice of Reasons for Rejection for Japanese Application No. 2019-545728, mailed Sep. 7, 2021 with translation, 7 pages.
Extended European Search Report for European Application No. 23165657.0, dated Jun. 16, 2023, 5 pages.

\* cited by examiner

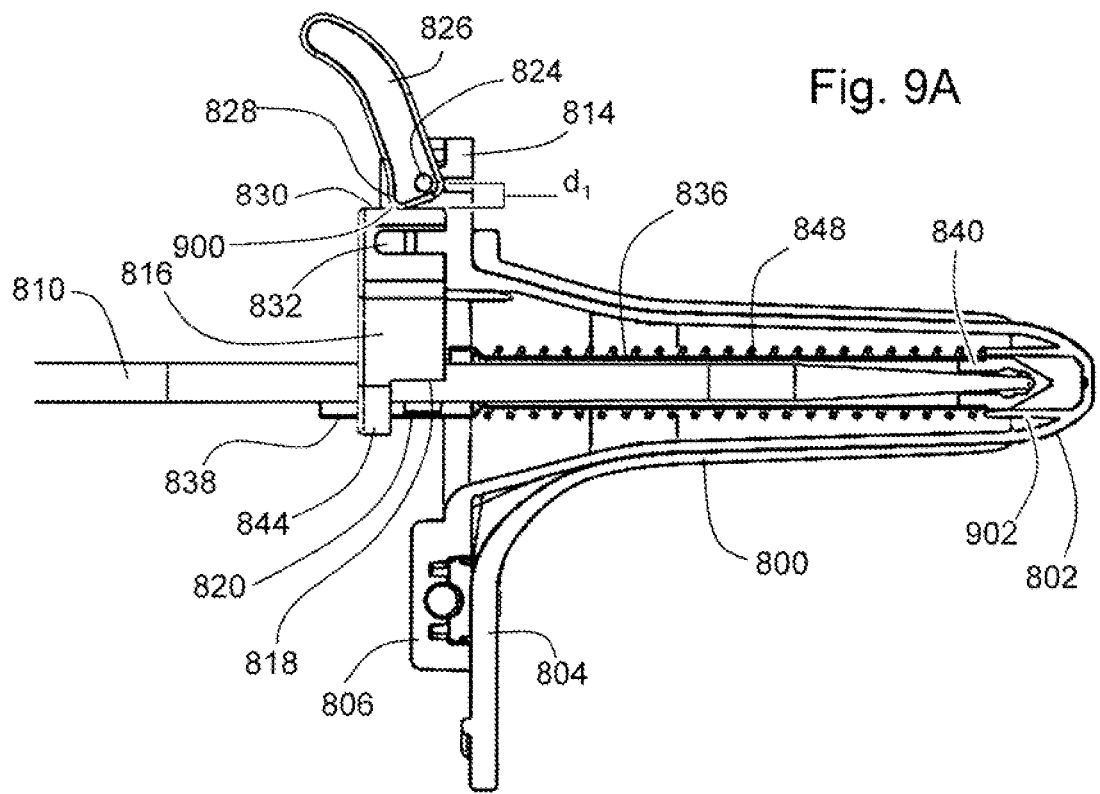
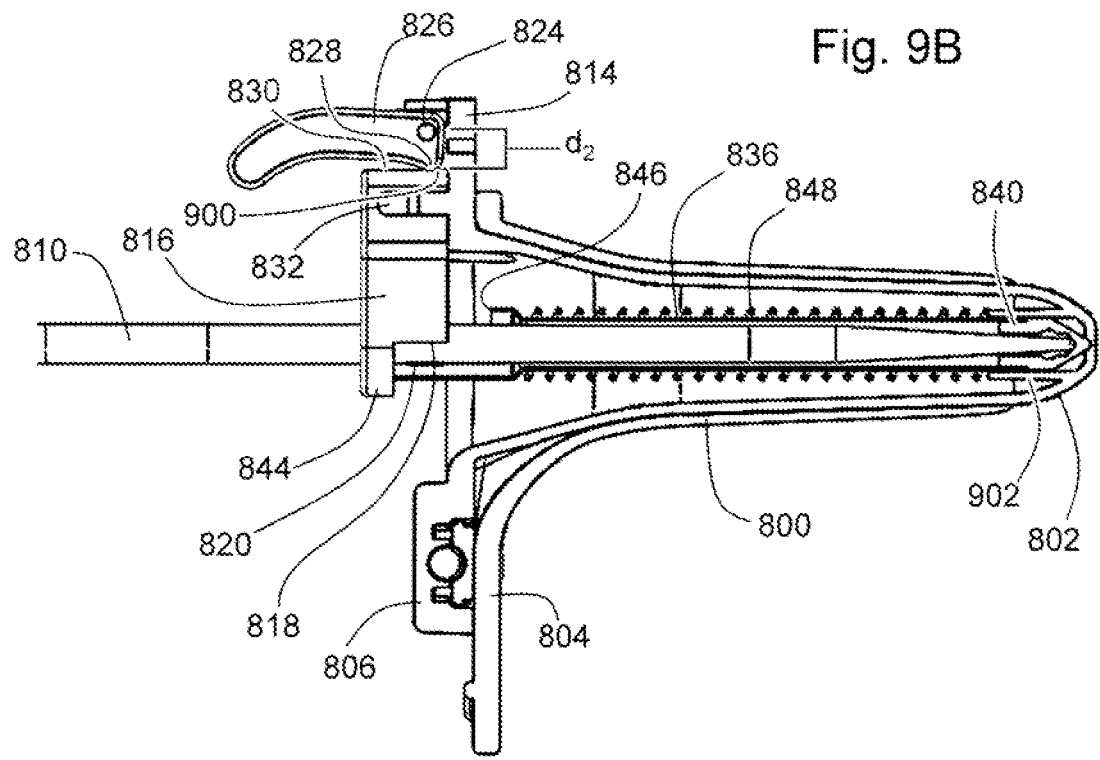

GUIDANCE SYSTEM MOUNTS FOR SURGICAL INTRODUCERS

CROSS-REFERENCE TO RELATED APPLICATIONS

This application claims priority as a continuation of U.S. application Ser. No. 16/369,848, filed on Mar. 29, 2019, which is a continuation of U.S. application Ser. No. 15/613,904, filed on Jun. 5, 2017, which is a continuation of U.S. application Ser. No. 14/711,305, filed on May 13, 2015, which claims the benefit of and priority to U.S. Provisional Application No. 61/992,378, filed on May 13, 2014. All of the foregoing applications are incorporated herein by reference in their entireties.

FIELD OF THE INVENTION

The present invention relates to surgical retractor systems and apparatus for securely connecting guidance system components to such retractor systems. The present invention also relates to apparatus for indicating when a guidance system component is in proper registration with a surgical introducer.

BACKGROUND

A variety of different devices have been used to retract delicate tissue during surgical procedures. One such device is illustrated in United States Patent Publication Number 2010/0010315 ("Mangiardi I"), which is incorporated herein by reference in its entirety. Mangiardi I shows two general versions of a retractor for delicate tissue. One version is a closed-channel retractor in the form of a tube (see, e.g., Mangiardi I FIG. 3), and the other is an open-channel retractor in the form of a curved channel (see, e.g., Mangiardi I FIG. 23).

FIG. 1 of this application illustrates a soft tissue retractor system such as found in Mangiardi I. The retractor system includes a hollow retractor 100, and an introducer 102 that is selectively inserted into the retractor 100. The retractor 100 and/or introducer 102 may include a handle 104 to facilitate manipulation and placement of the retractor system, and a lock to hold the introducer and retractor together. The illustrated handle 104 is molded integrally with the retractor 100, but it may be a separate part. The handle 104 may be configured to connect to a clamp 106, such as the standard surgical clamp 106 shown in FIG. 1. In this example, the handle 104 has a ridge 108 that fits into a corresponding groove 110 on the clamp 106, to prevent relative rotation between the two when engaged. Modifications to this design are described in Mangiardi I.

A retractor system such as shown in FIG. 1 is often used by inserting the introducer 102 into the retractor 100 and locking it in place, so the two can be moved and manipulated as a unit. The combined retractor system is inserted into the patient's body and moved to the surgery site, and then the introducer 102 is unlocked and removed to permit access to the site through the retractor 100. When the unit is in place (either before or after the introducer 102 is removed), the handle 104 may be locked to a clamp 106 to hold the retractor 100 in place. An example of this procedure is shown in FIGS. 16-20 of Mangiardi I. Surgeons using the Mangiardi I retractor sometimes do not use a clamp to hold the retractor at the surgery site, and often manually manipulate the retractor to access different parts of the surgery site during the surgical procedure. The retractor system and the retractor may be manipulated by holding the proximal ends of the introducer or retractor or by holding the handle.

The device shown in Mangiardi I may have a transparent introducer 102 and/or retractor 100, and surgeons using such devices advantageously use the transparent introducer and retractor to manually guide the unit to the surgery site. While it has been found that visual guidance by looking through the introducer 102 is very beneficial, it also has been found that some form of additional guidance or navigation may be desired in some cases. For example, in some cases, surgeons have used a probe or guide wire (a narrow elongated rod) to guide the movement of the retractor system. In such cases, the probe is advanced to the surgery site, and then the interlocked retractor system is slid over the probe until it reaches the surgery site. This is facilitated by the inclusion of a hole at the tip of the introducer that fits around the probe. If the hole through the tip of the introducer is absent, this method cannot be used. This type of system is described in United States Patent Publication Numbers 2008/0109026 and 2009/0048622, which are incorporated herein by reference. These references also show an alternative construction, in which the retractor is not locked to the introducer.

It has been found that some surgeons using the above procedure may use a probe that is integrated into a computer navigation system. For example, the probe may include a so-called "starburst" or the like, on the probe's proximal end (i.e., the end opposite the distal end that is inserted to the surgical site). This and other navigation systems are known in the art. For example, frameless navigation systems and other computerized guidance systems and methods are described in U.S. Publication No. 2001/0027271 (which is incorporated herein by reference in its entirety) and others, and are commercially available from companies such as Medtronic, Inc., Stryker, BrainLab, AG, and GE Healthcare. As used herein, "computerized guidance" encompasses any method of guiding a device to or at a surgical site that relies on computer visualization and/or control. Mangiardi I briefly notes the possibility of using stereotactic guidance or navigation in conjunction with a surgical retractor, but does not illustrate or describe this procedure or any apparatus for accomplishing this objective.

While computerized surgical guidance systems are well-known, a number of limitations exist with respect to their use with retractor systems, and particularly with systems like those shown in Mangiardi I. For example, while some surgeons use computerized guidance to direct a probe to the surgery site, and then slide the retractor system over the probe to the site, the movement of the retractor may be somewhat imprecise and the process can be unduly cumbersome. This method also is not available if the retractor system does not have a through-hole that fits over the probe (due either to the absence of a hole or a hole that is too small). In addition, the probe does not provide a view of the tissue through which it is advanced, so there is no visual means to perceive and avoid critical tissue (e.g., major blood vessels or nerves) when inserting a probe before inserting a retractor/introducer system. Also, the small-diameter probe may sever delicate tissue cells, such as grey or white brain matter, rather than moving the cells aside and passing between them as would be expected to happen when advancing the retractor system.

United States Patent Publication Number 2013/0066154 ("Mangiardi II"), shows examples of systems for integrating a navigation probe into a surgical introducer. For example, FIGS. 1-6 of Mangiardi II shows a navigation probe that is secured to the inside of a pre-existing introducer by resilient means, such as rubber plugs or O-rings. Another version of the Mangiardi II device uses a slip fit (e.g., FIGS. 7-8), and still another version uses an arm to hold the probe down inside the introducer (FIG. 9). Still other versions mount the navigation device outside the introducer, to an arm that is connected to the retractor assembly (FIGS. 10-11). While these systems may provide suitable performance, they also have certain potential shortcomings. For example, resilient plugs may slip in the presence of fluids, a slip fit requires careful monitoring to ensure proper positioning, an arm as shown in FIG. 9 to hold the probe in place requires the probe to be modified to include a surface against which the arm pushes, and locating the navigation device outside the introducer complicates the correlation between the navigation device and the tip of the introducer or retractor.

United States Patent Publication Number 2012/0071748 shows another example of a system for integrating a navigation probe into a surgical introducer. In this case, the probe is retained in a narrow channel through the introducer, and held in place with a threaded locking screw. The locking screw adds an additional potentially-removable part to the operating theater, and therefore this reference adds a separate retaining device (see FIG. 7B) to prevent the locking screw from being removed.

It has been found that there still remains a need to provide alternative apparatus and methods for coordinating the use of guidance systems with surgical introducers.

SUMMARY OF THE INVENTION

In one aspect, there is provided a delicate tissue retraction system for use with a navigation probe having a probe shaft and a probe tip at a distal end of the probe shaft. The delicate tissue retraction system includes a retractor and an introducer. The retractor has a hollow tubular retractor passage extending along a longitudinal axis from a proximal retractor end to a distal retractor end. The introducer has an introducer wall forming an introducer channel extending from a proximal introducer end to a distal introducer end. The introducer is configured to be removably installed within the retractor such that the proximal introducer end and distal introducer end are located along the longitudinal axis and the distal introducer end extends beyond the distal retractor end. The introducer has a mount integrally formed with the introducer and extending from the distal introducer end into the introducer channel. The mount is positioned to surround the probe tip when the navigation probe is at a fully inserted position within the introducer with the probe tip at the distal introducer end.

In some aspects, the mount may have an outer mount wall surrounding the mount and extending along and facing an adjacent inner portion of the introducer wall.

In some aspects, the mount may have a plurality of ribs. The ribs may each have an outer wall extending along and facing an inner portion of the introducer wall. The distal introducer end may terminates at an introducer tip, and have an opening extending through the introducer tip. The ribs may surround the introducer tip.

In some aspects, the mount may have a ring-shaped wall extending from the introducer wall into the hollow introducer channel. The ring-shaped wall may have an inner surface extending parallel to the longitudinal direction. The ring-shaped wall may have an outer surface extending along and facing an inner portion of the introducer wall. The outer surface may extend parallel to the longitudinal direction. The ring-shaped wall may have an inner surface extending parallel to the longitudinal direction. The distal introducer end may terminate at an introducer tip having an opening extending through the introducer tip. The mount may surround the introducer tip. The mount may surround a geometric centerline of the introducer.

In some aspects, the distal introducer end may terminate at an introducer tip, and there may be an opening extending through the introducer tip, and the mount may surround the introducer tip.

In some aspects, the distal introducer end may terminate at an introducer tip located along the central geometric axis of the introducer.

In some aspects, at least a portion of the introducer wall may be a transparent material, and the hollow introducer channel and the probe shaft receptacle may be dimensioned to allow visualization between the hollow introducer channel and the probe shaft receptacle, along the introducer channel, and through the transparent material.

Some aspects may include a clamp configured to hold the probe shaft with the probe tip at a position where it is surrounded by the mount. The clamp may extend into the hollow introducer channel at the proximal introducer end. The mount may extend towards the clamp, with a gap between the mount and the clamp.

The foregoing summary of the invention provides a variety of exemplary embodiments that may be used in any suitable combination, and is not intended to impose any limitations upon the invention recited in the claims.

BRIEF DESCRIPTION OF THE DRAWINGS

A better understanding of the exemplary embodiments may be understood by reference to the attached drawings, in which like reference numbers designate like parts. The drawings are exemplary, and not intended to limit the claims in any way.

FIG. 9A is a cutaway side view of the embodiment of FIG. 8, shown with the probe partially installed and the clamp in the unclamped position.

FIG. 9B is a cutaway side view of the embodiment of FIG. 8, shown with the probe fully installed and the clamp in the clamped position.

BRIEF DESCRIPTION OF EMBODIMENTS

Embodiments of the invention may provide various features to supplement or advance the state of the art of surgical introducers and retractor systems. For example, embodiments may extend the capability of conventional surgical retractors by proving a system to securely hold a guidance system probe or by providing an indicator to identify when the probe is not properly positioned. As used herein, the term "guidance" is intended to include any system for assisting a surgeon with advancing the retractor system to the surgery site, and can include passive systems like guide wires, or active systems like navigation probes that are detected and tracked using a computerized telemetry system. (The term "surgeon" includes anyone in the operation theater who might use or manipulate the introducer system.) Active probes can be tracked optically by a "starburst" or other marker mounted on a portion of the probe that remains visible during the procedure, by directly monitoring the tip of the probe using radiation imaging (e.g., X-ray) or magnetic imaging, by physically connecting the probe to a frame of reference system to mechanically track the position of the probe, or by other means or combination or means, as known in the art. The terms "navigation" and "guidance" are used interchangeably herein. Embodiments also may be used with manual systems in which the surgeon moves the retractor system entirely by hand, or semi-automated or automated systems that operate under the surgeon's control or automatically advance the retractor system to the surgery site without the surgeon's intervention.

Figure 1:
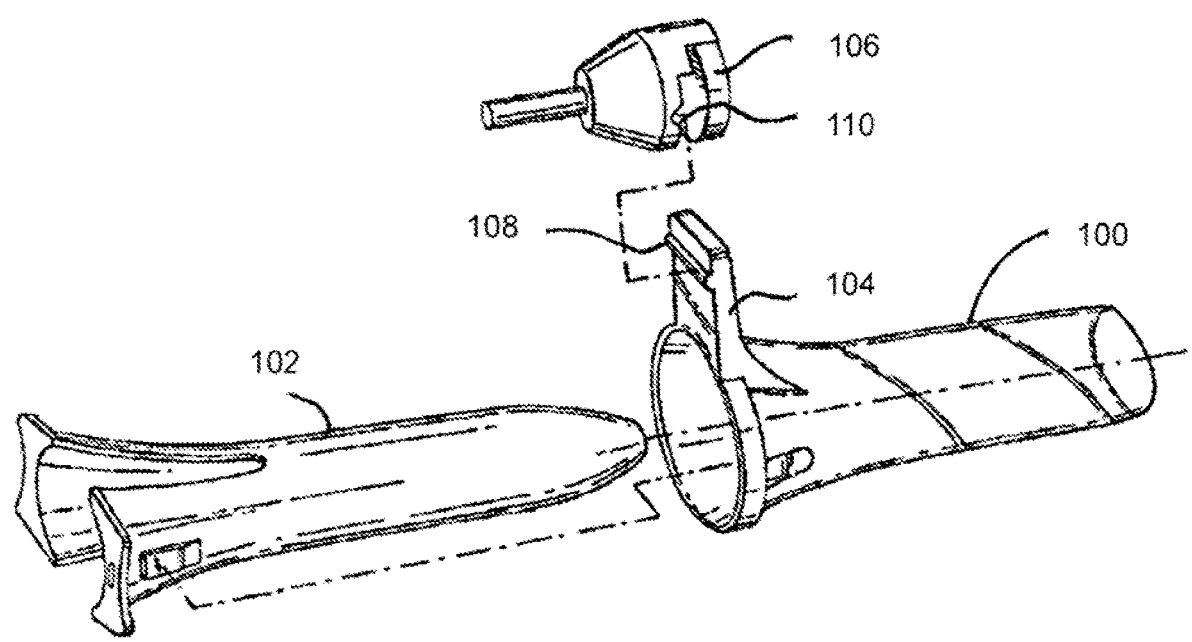
FIG. 1 is an example of a prior art delicate tissue retractor system.

Embodiments may be used with dedicated systems that are designed anew, or with preexisting systems. For example, embodiments may be used with systems like the one shown in FIG. 1, such as by supplementing, modifying or replacing the introducer 102, or with other introducer assemblies, as will be appreciated by persons or ordinary skill in the art. The following embodiments described herein may be used with a retractor 100 as shown in FIG. 1, or in other retractors. It will be readily appreciated that the shape of the introducer can be modified to fit into any conventional retractor, and the introducer also may be modified to connect to the retractor (if necessary or desired) using any suitable clamp or other engagement mechanism. For example, embodiments may be used with small-scale versions of introducers like the one shown in FIG. 1, in which the embodiment optionally may be scaled down to allow visibility into the retractor, but providing such visibility is not required in all embodiments.

The exemplary embodiments described herein are directed towards introducers for use in neurosurgery or other operations in and around the brain or skull. However, uses in other parts of the body are also possible.

Figure 2:
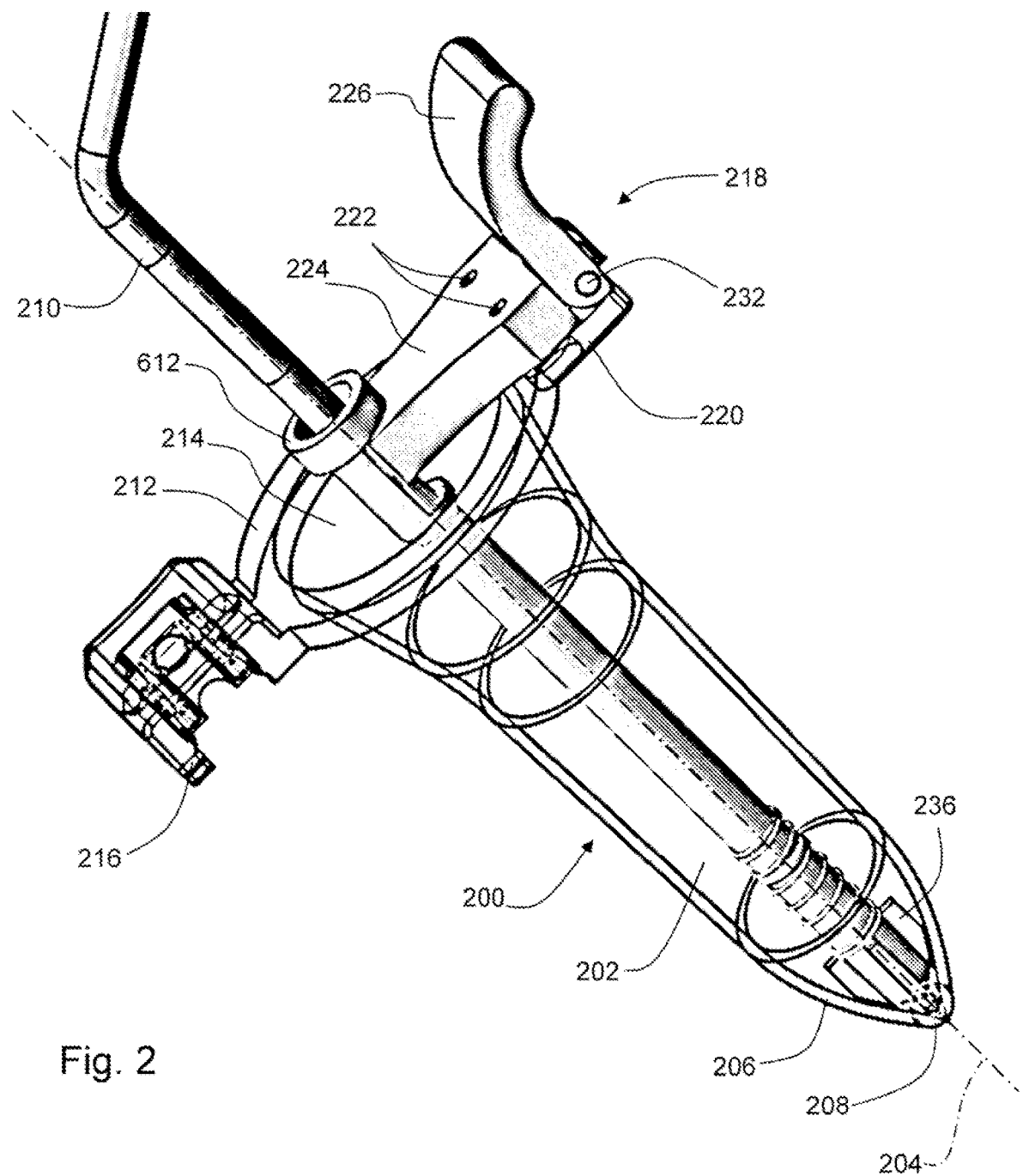
FIGS. 2 and 3 show an embodiment of an introducer, clamp, and navigation probe, with the clamp in the clamped and unclamped positions, respectively.

FIG. 2 shows an exemplary embodiment of an introducer 200 that is configured to releasably connect with a navigation probe 210. The introducer 200 is configured to fit into a conventional retractor, such as those shown in FIG. 1 or those otherwise available from Vycor Medical of Boca Raton, Florida, but other retractors—such as custom-built retractors—may be used.

The introducer 200 is constructed as a hollow channel 202 that extends along a longitudinal axis 204. The channel 202 may be closed (i.e., without perforations or openings, but alternatively may include openings through the sidewall of the channel 202. The channel 202 may have a curved cross-section as viewed along the longitudinal axis 204. Such a curved cross-section may be circular, elliptical, oval or otherwise generally curved (i.e., comprised entirely of curved surfaces and/or very short straight surfaces that effectively simulate a smoothly-curved shape). If desired, the cross-section may include one or more rectilinear segments (e.g., a D-shape), or may be entirely rectilinear (e.g., a square or triangular shape). The cross-section of the channel 202 also may taper to be larger at one end than the other, and preferably reduces slightly in size as it approaches the distal end 206 of the introducer. The retractor 100 may be shaped to match the shape of the introducer, and particularly the channel 202, as known in the art, however, it is not strictly required for the introducer 200 and retractor 100 to have matching geometric shapes.

The distal end 206 of the introducer is the end that is inserted into the tissue. The distal end 206 transitions (preferably smoothly) from the cross-sectional shape of the channel 202 to a tip 208. The shape of the transitional region may be linear or curved, as viewed from a direction perpendicular to the longitudinal axis 204. A linear transition would appear generally like an angular wedge, whereas a curved shape would appear as a wedge with bulging sides (e.g., "bullet"-shaped). The transition also may be stepped or rectilinear (i.e. an abrupt termination at a flat tip 208), but these versions may be less preferred.

The tip 208 may be closed to prevent the ingress of fluid or material into the channel 202, or it may be open by including a small opening. If used, an opening preferably has rounded or squared-off edges corners to prevent cutting of tissue as the introducer 200 is advanced through the tissue. In conventional introducers (e.g., those shown in Mangiardi I), an open tip can be desirable to allow a surgeon to remove tissue as the introducer is advanced. However, the placement of the probe 210 in the channel 202 may make this use impossible, and therefore a closed tip 208 may be preferred. However, it still may be desirable to include an opening at the tip 208 to allow gas or fluid to be removed (or introduced) in some applications.

The proximal end 212 of the channel 202 terminates at an opening 214 that is configured to receive the probe 210, and also may be sized to allow visual inspection into the channel 202. Visual inspection may be desirable to help the surgeon visualize the underlying tissue through a transparent distal end 206 of the introducer 200 or through transparent sidewalls of the channel 202. The introducer 200 may be provided with transparent portions by forming the introducer from a transparent material (e.g., polycarbonate), adding transparent windows to an otherwise opaque material, or providing uncovered openings through the material. Portions or all of the retractor 100 also may be transparent (e.g., transparent polycarbonate), to allow visualization through the combined retractor assembly. Other embodiments may not have a transparent introducer 200, in which case the need to make the opening 214 large enough to allow visualization is not necessary. The opening 214 also may be sized to allow the introduction of one or more other surgical instruments or apparatus, such as suction hoses, resectors, cauterizers, scopes, or the like.

The introducer 200 also may include an introducer connector 216 to connect the introducer 200 to a retractor 100, as known in the art. The introducer 200 may be disposable or reusable. The introducer 200 may be made of any material or materials suitable for surgical applications, such as sterilized polycarbonate, stainless steel, or the like. The introducer 200 also may be coated with chemicals, such as a lubricating film, anti-coagulants or the like. Portions of the introducer 200 that may reflect lights during surgery may be coated with anti-reflective paints or coatings, or be surface treated (roughened or knurled) to help reduce strong glare, as known in the art.

The probe 210 may be specially-designed to engage with and work with the introducer 200, or it may be a pre-existing or otherwise available probe. The probe 210 preferably is a reusable device, but this is not strictly required. Examples of probes that may be used with embodiments of the invention are available from BrainLab AG of Feldkirchen, Germany, but other navigation probes may be used. The probe 210 may be used in conjunction with other navigation or surgical instruments, such as a navigation reference array, a probe manipulation arm, or other devices.

The probe 210 is secured to the introducer by a clamp mechanism 218. The clamp mechanism 218 preferably is configured to securely hold the probe 210 without damaging the probe 210. It is also preferable that the clamp mechanism 218 can be operated easily by the surgeon. To this end, the clamp mechanism 218 may be a single-action clamp that is configured to be operated by a single movement of the clamp actuating mechanism. For example, the clamp mechanism 218 may comprise a lever that requires movement from one position to another by a single movement of the surgeon's hand, such as extending or retracting a thumb or finger, to engage the probe. However, two handed operation may be desirable or possible in other embodiments, and an embodiment that facilitates single-motion operation is not necessarily intended to prohibit manipulation by other movements.

Referring to FIGS. 2-5B, the exemplary clamp mechanism 218 is attached at one side of the proximal end 212 of the introducer channel 202. In this case, the introducer 200 includes a clamp mounting flange 220 that extends outward from the channel 202, and the clamp mechanism 218 is secured to the flange 220 by connectors such as pins, rivets, screws, bolts, welding (e.g., ultrasonic welding), adhesives, or other known means. For example, the clamp mechanism 218 may be connected to the flange by two mounting screws (not shown) that pass through holes 222 and into corresponding holes through the flange 220. Using this arrangement, the clamp mechanism 218 may be mounted to introducers of various shapes and sizes by adding a suitably-sized mounting flange to each different introducer. In other embodiments, the clamp mechanism 218 may be formed integrally with the introducer 200. In still other embodiments, the flange 220 may be omitted and other mechanisms for attaching the clamp mechanism 218 to the introducer 200 may be used. For example, the clamp 218 may be connected to a conventional introducer, by a band clamp that wraps around the perimeter of the proximal end of the introducer or by an expanding clamp that engages the inner surface of the introducer. Other alternatives will be readily apparent to persons of ordinary skill in the art in view of the present disclosure.

The exemplary clamp mechanism 218 includes a main body 224, a control member in the form of a clamp lever 226, and a clamp in the form of a tension band 228 (FIG. 4) and anvil 230. The main body 224 protrudes radially inwards towards the centerline of the channel 202 and terminates at the anvil 230 at the inner end of the main body 224. The anvil 230 may be shaped to receive the probe 210 in a notch. The notch may be shaped to complement the shape of the probe 210 to help precisely position the probe 210. A notch that has tapered or converging walls may be preferred because it helps center the probe 210 as the tension band 228 is tightened around the probe 210. For example, the anvil 230 may comprise a V-shaped notch (as shown) that extends parallel to the longitudinal axis 204. Other notch shapes, such as a U-shaped notch or a square notch, may be used in other embodiments. The anvil 230 also may comprise a flat face, which can also help to effectively position the probe 210 at a desired position if the tension band 228 is suitably shaped.

Collectively, the tension band 228 and the anvil 230 form a clamp that is axially aligned with the introducer channel 202. Thus, the clamp is able to hold the probe 210 within the introducer 200. The clamp preferably is located to position the probe 210 along the longitudinal centerline 204, and preferably at the central geometric axis, of the introducer 200.

Figure 3:
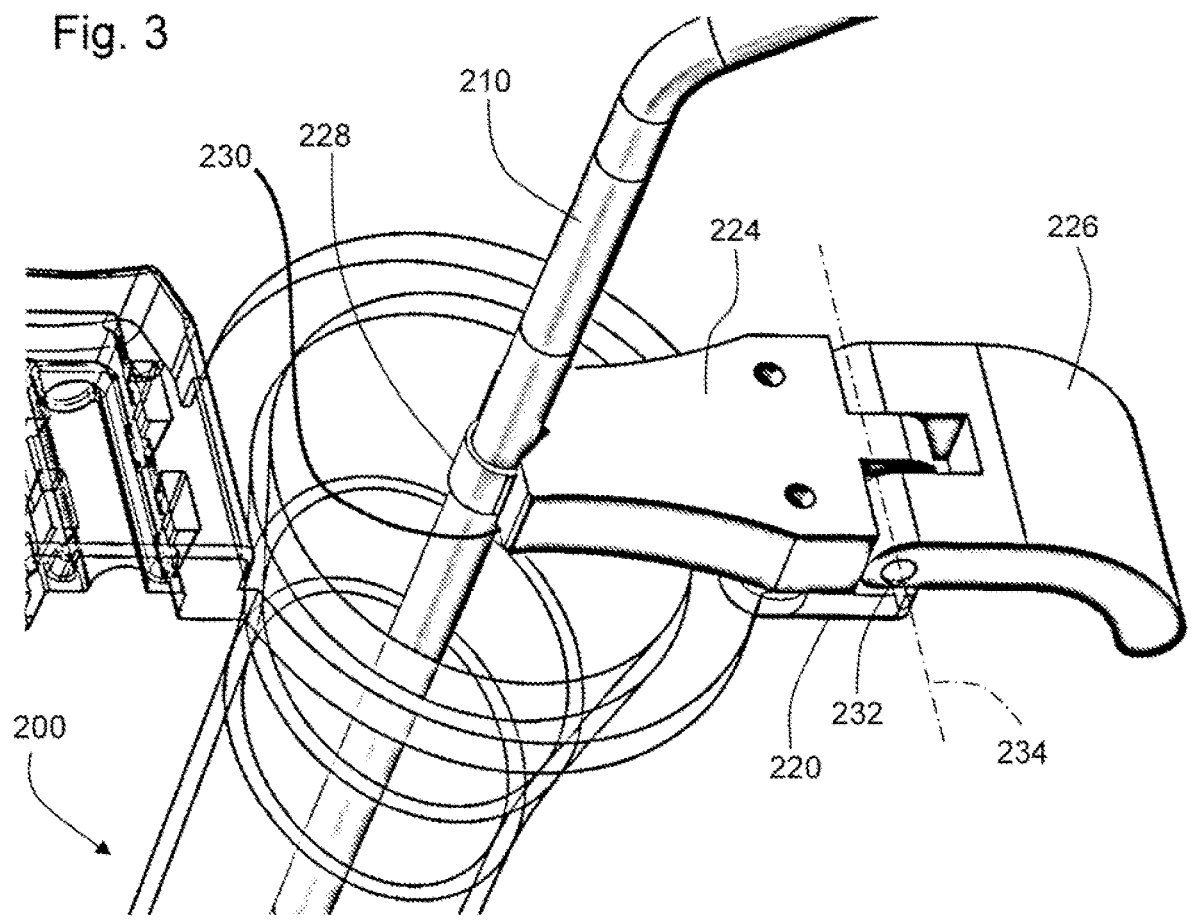
Figure 4:
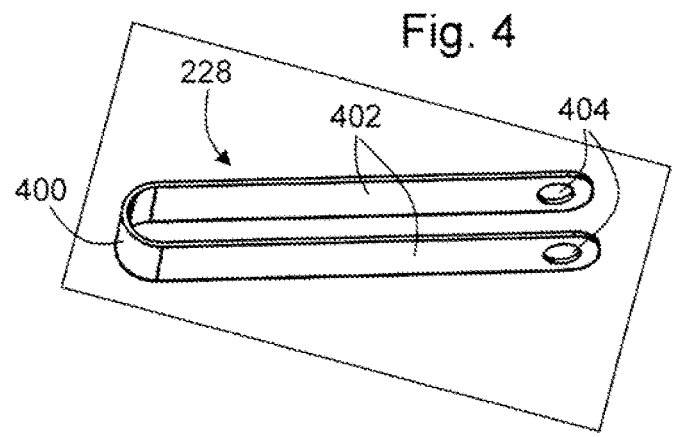
FIG. 4 shows an example of a tension band that may be used with embodiments of the invention.
Figure 5A:
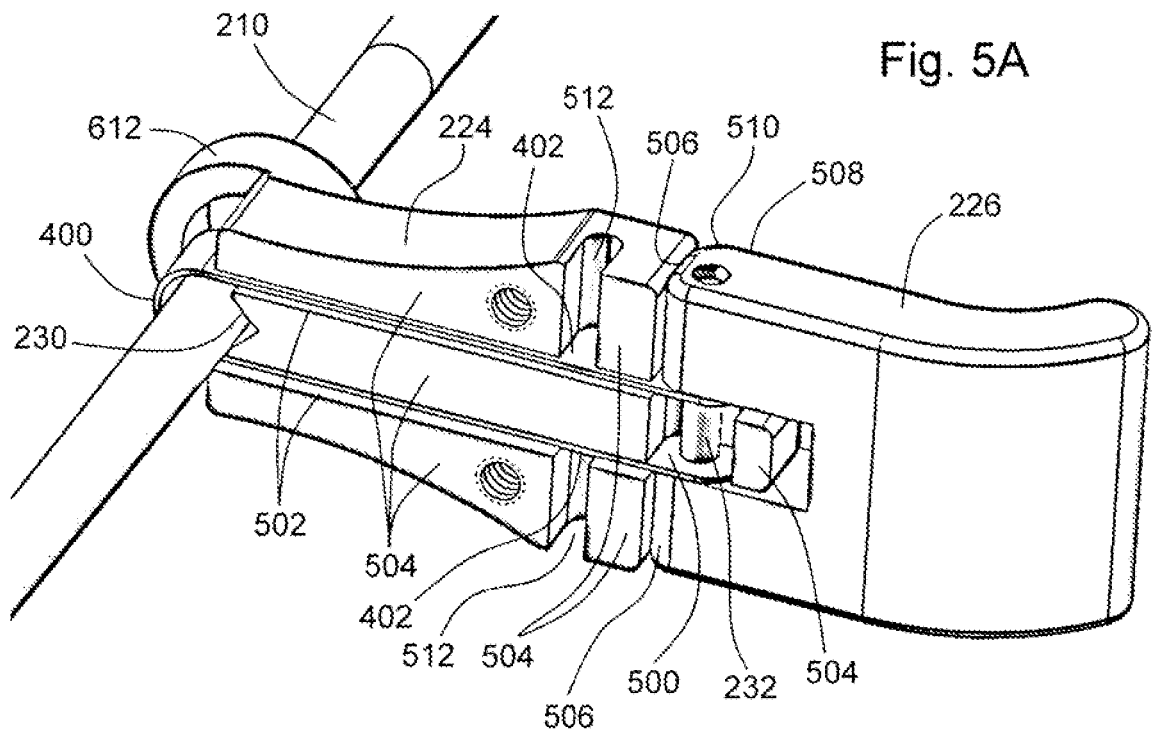
FIGS. 5A and 5B show another example of a clamp in the unclamped and clamped positions, respectively.
Figure 5B:
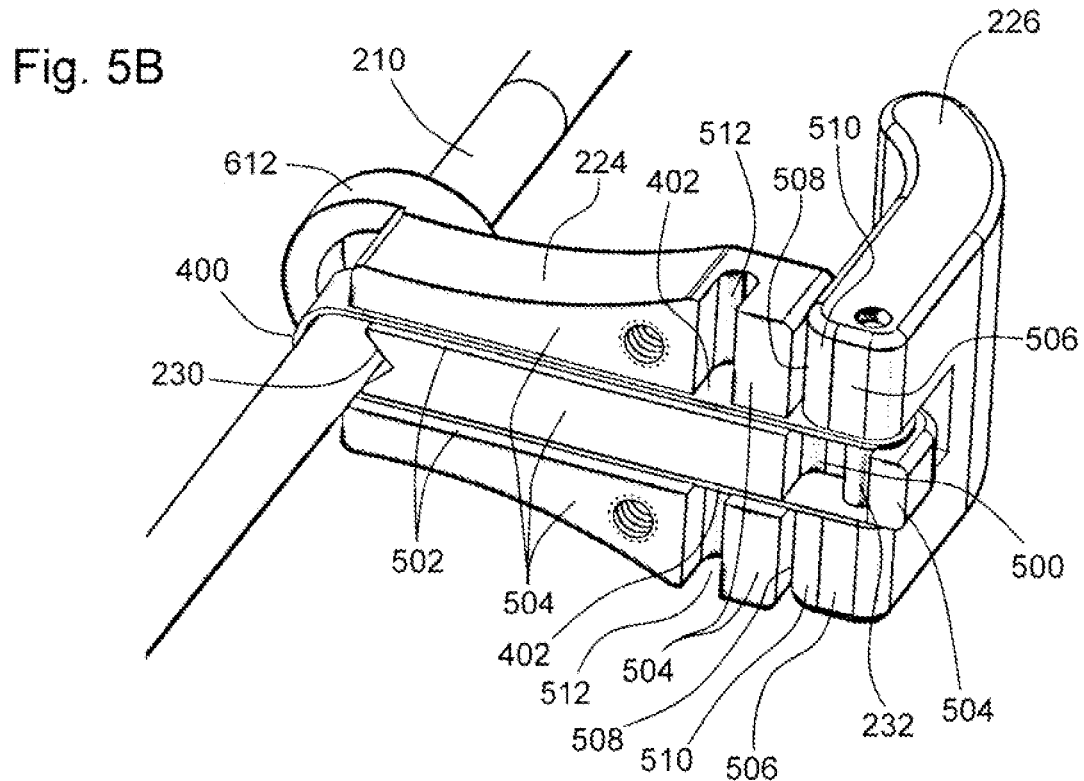

The clamp lever 226 may be connected at the outer end of the main body 224 by a pin 232 that fits within a slot 500 (FIG. 5A-B), or by other pivoting or moving connectors such as integral pins, bosses, or slotted features to connect to the main body 224. In the embodiment shown, the pin 232 allows the clamp lever 226 to rotate relative to the main body 224 about a pin axis 234. The clamp lever 226 and the adjacent parts preferably are shaped so that the clamp lever 226 has a limited rotational range of motion. For example, the clamp lever 226 may be movable through a range of motion of about 90° between an unlocked position shown in FIGS. 3 and 5A, and a locked position shown in FIGS. 2 and 5B. The clamp lever 226 may have any shape, such as a curved shape, an angled shape, or a straight shape. A curved or angled shape may be helpful to assist the surgeon with gripping and moving the clamp lever 226. In FIGS. 2-3, the clamp lever 226 is curved downward, but the clamp lever 226 instead may be curved upward as shown in FIGS. 5A-B. Additional structures and operation of the clamp lever 226 are described in more detail below.

The tension band 228 may comprise a strip of material (e.g., stainless steel, elastomeric compound, plastic, or the like) that is bent to form a loop 400 and two arms 402. Each arm 402 includes a respective hole 404. The tension band 228 is movably associated with main body 224, such as by positioning the arms 402 to slide within respective channels 502 through the main body 224. The pin 232 passes through the two holes 404 to connect the arms 402 to the clamp lever 226. When the parts are assembled, the loop 400 is located proximate to the anvil 230, and movement of the clamp lever 226 causes the loop 400 to move towards and away from the anvil 230. Thus, the loop 400 and the anvil 230 form the two operative parts of the clamp mechanism. It will be readily appreciated that the tension band 228 also may comprise alternative structures, such as a unitary molded plastic part or an assembly of parts (e.g., a separate molded plastic loop 400 with connected metal arms 402). Other alternatives will be readily apparent to persons of ordinary skill in the art in view of the present disclosure. A single arm 204 also may be used in other embodiments; for example, the tension band 228 may comprise a "J-shaped" member having a loop 400 and a single arm 402. The term "tension band" is intended to include any structure that can be moved against the anvil to hold the probe 210 in place.

FIGS. 5A and 5B show the clamp lever 226 in the unlocked and locked positions, respectively. In these figures, the flange 220 is removed to show the underside of the main body 224 and other parts. When the parts are installed, some or all of the lower surface 504 (or portions thereof) or other parts of the main body 224 contact the flange 220 to connect the clamp mechanism 218 to the introducer. Such connection may be direct, or through an intermediate part, such as an adhesive layer, a gasket, another functional part, and so on. The slot 500, in which the pin 232 is located, is formed by an arch-like portion of the main body 224 that extends between two parts of the lower surface 504. When the main body 224 is connected to the flange 200, the pin 232 is captured in place within the slot 500, but movable within the slot 500 towards and away from the anvil 230. Similarly, the arms 402 of the tension band 228 are captured within their respective channels 502. It will be appreciated that other embodiments may form the slot 500 or channels 502 in other parts (e.g., in the flange 200), and the main body 224 may comprise multiple assembled parts instead of an integral unit. It is also envisioned that the arms 402 may extend partially or entirely outside the main body 224, instead of being captured in channels 502 as shown.

As noted above, the clamp lever 226 is shaped to rotate through about 90° between the unlocked position in FIG. 5A, and the locked position in FIG. 5B. The clamp lever 226 includes an integrated cam mechanism comprising a first face 506 and a second face 508. In the unlocked position, the first face 506 of the clamp lever 226 faces the adjacent portion of the main body 224, and in the locked position, a second face 508 of the clamp lever 226 faces the adjacent portion of the main body 224. The first and second faces 506, 508 are positioned at different distances from the pin axis 234. More specifically, the first face 506 is relatively close to the pin axis 234, and the second face 508 is relatively far from the pin axis 234. Thus, the first and second faces 506, 508 form a cam surface with respect to the pin axis 234. In this arrangement, the pin 232 can move relatively close to the anvil 230 when the clamp lever 226 is in the unlocked position, which allows the loop 400 of the tension band 228 to move further away from the anvil 230. When the clamp lever 226 is moved to the locked position, the second face 508 moves between the pin 232 and the abutting surface of the main body 224, and forces the pin 232 to move further away from the anvil 230. This causes the pin 232 to pull back on the tension band 228 to move the loop 400 closer to the anvil 230. This movement locks the probe 210 in place between the loop 400 and the anvil 230.

A transition surface 510 of the clamp lever 226 that connects the first face 506 to the second face 508 may be rounded to ease movement between the unlocked and locked positions. The transition surface 510 also may include a portion that is even further from the pin axis 234 than the second face 508, which will prevent movement from the locked position to the unlocked position without first applying an additional force to move past the transition surface 510. For example, in the shown embodiment, the first and second surfaces 508, 510 are flat surfaces that fit flush to the main body 224, and the transition surface 510 comprises a rounded lobe. The use of the flat surfaces, and particularly forming the second face 510 as a flat surface as shown, also provides a more positive feel to assure the surgeon that the clamp lever 226 is in the desired position.

While the foregoing latch arrangement is preferred for its ease of use and positive engagement and disengagement operation and feel, other embodiments may use other mechanisms or means to hold the clamp lever 226 in the locked position. For example, a spring-loaded latch may be used to hold the clamp lever 226 in the locked position, and upon releasing the latch the tension in the tension band 228 may cause the clamp lever 226 to move back towards the unlocked position.

The slot 500 may be sloped to press the pin 232 downward—that is, towards the tip 208 of the introducer 200—as the pin 232 moves away from the anvil 230 to place the tension band 228 into the locked position. To accomplish this, the slot 500 could be sloped so that the far end of the slot 500 (i.e., the end most distant from the anvil 230) is closer to the introducer tip 208 with respect to the longitudinal axis 204 than the near end of the slot 500. In this arrangement, a vertical force may be generated through a slight downward movement of the tension band 228 to urge the probe 210 towards the tip 208 of the introducer 200. This may be beneficial to help place the probe in the fully-seated position during latching.

The tension band 228 may comprise any material suitable for engaging and holding the probe 210 in place. For example the tension band 228 may comprise spring steel, a loop of plastic or composite material, an elastic band, or other materials. In one embodiment, the tension band 228 may comprise a strip of stainless steel that is 0.140 inches wide by 0.020 inches thick having 0.0625 inch diameter holes and a loop 400 with a radius of 0.069 inches. The foregoing values are approximate, and a reasonable range of dimensional values that still provide the essential function of the tension band 228 could, of course, be used for this particular embodiment. Different values for these dimension could be used in other embodiments, and, as noted above, the tension band 228 may comprise alternative constructions or shapes. Any suitable shape or construction may be used to provide a tension band 228 that act as a clamp to hold the probe 210 against the anvil. The design of alternative tension bands having alternative materials and/or dimensions will be within the skill of ordinary persons in the art, without undue experimentation, in view of the present disclosure, and in view of the sizes and shapes of available probes 210.

The remaining parts of the clamp mechanism 218 may be made of any suitable material or materials. In one example, the main body 224 and the clamp lever 226 comprise molded polycarbonate, ABS plastic, cast or machined metal, or the like.

Preferably, at least one part of the assembly will flex in order to generate a restoring force to clamp the probe 210 firmly between the tension band 228 and the anvil 230. For example, the tension band 228 (particularly the sections surrounding the holes 404) may stretch slightly to generate a restoring force. The tension band 228 may have corrugations, slots, or other features to adjust its spring rate, and provide a larger tolerance range for clamping the shaft of the probe 210. Other parts that may flex include the pins 232, the anvil 230 (or other parts of the main body 224), the clamp lever 226, or the probe 210 itself. Additional parts also may be added to provide a resilient restoring force. For example, a strip of pliable rubber or other flexible material may be provided on the loop 400 or anvil 230. Such material may also provide frictional grip to help prevent the probe 210 from sliding in the longitudinal direction 204. For simplicity, the clamp mechanism 218 may be designed such that one part is particularly designed to provide the flexure necessary to generate a restoring force, and flexure of the remaining parts can be considered nominal. For example, the tension band 228 dimensions may be modified until the desired clamping force (or range of forces) is obtained. As another example, the main body 224 may include a resilient structure formed by cutouts 512, which allow the portion of the main body 224 against which the second face 508 of the clamp lever 226 abuts to flex relative to the rest of the main body 224 to provide a resilient force to hold the tension band 228 in tension.

The clamping force is required only to prevent unwanted movement of the probe 210 during normal surgery conditions, and it is expected that the typical forces that would be applied during surgery that could separate the probe 210 from the introducer 200 will be less than four (4) pounds. Persons of ordinary skill in the art of mechanical design will be able to construct the clamp mechanism 218 to hold the probe 210 with any desired amount of holding force without undue experimentation.

The clamp may be configured to be operated during a surgical procedure, and preferably can be operated with one hand. For example, the surgeon using this embodiment can hold the introducer 200 by looping the middle finger below the introducer connector 216, looping the index finger below the flange 220, and pushing or pulling on the clamp lever 226 with the thumb. With the other hand, the surgeon can hold the probe 210 or other objects. This allows the surgeon to hold the introducer 200 in place while locking or unlocking the clamp mechanism 218 to remove, adjust, or install the probe 210 during a surgical procedure. The range of movement of the clamp lever 226 may be adjusted as desired, but it is preferably for the clamp lever 226 to rotate through a range of about 90° or less, in order to simplify and ease operation between the clamped and unclamped positions.

The clamp mechanism 218 also may be configured to minimize obstructing the surgeon's visual or physical access through opening 214. For example, the side walls of the main body 224 may converge as they approach the anvil 230, and the anvil 230 and loop 400 may be made only large enough as needed to hold the probe 210. This minimizes the size of the clamp mechanism 218, as viewed along the longitudinal direction, and helps the surgeon look down into or pass instruments into the channel 202.

Figure 6:
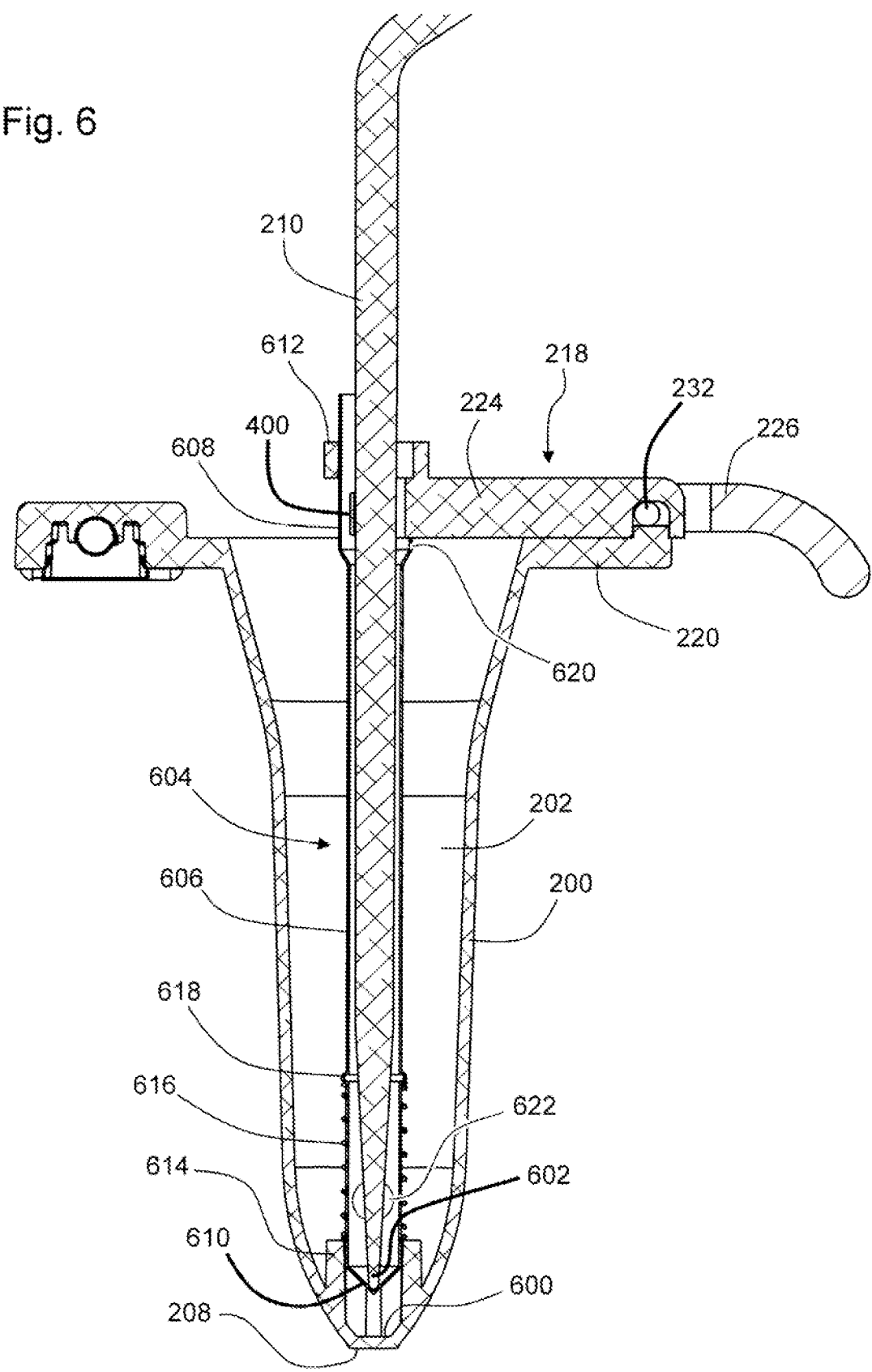
FIG. 6 is a cross-sectional view showing an exemplary introducer, clamp, navigation probe, and registration indicator.

Referring now to FIG. 6, the introducer 200 and clamp mechanism 218 assembly preferably includes a stop surface 600 that the probe's tip 602 contacts (directly or through an intermediate part) when the probe 210 is fully seated in the introducer 200 to place the probe 210 in the proper registration position. The registration position is the position at which the probe 210 is expected to be for purposes of using the probe 210 to accurately determine the position of the introducer 200. For example, the probe's tip 602 may be located at a known position in relation to the navigation system, and, if the probe tip 602 is located close to the distal tip 208 of the introducer 200, then the probe tip's position may be used as a nominal value for the location of the introducer tip 208. Alternatively, the system can be programmed, as known in the art, to account for the offset in locations between the probe tip 602 and the introducer tip 208, in which case the system can more accurately track the introducer tip's location (provided the probe tip 602 remains properly registered with the introducer 200).

Regardless of how the navigation system is programmed, it relies on a known spatial correlation between the probe tip 602 and the introducer's tip 208 (or whichever part of the introducer 200 is desired to be tracked). If the probe tip 602 is not advanced far enough into the introducer 200, then the introducer tip 208 will be offset deeper into the tissue than what the navigation system indicates. As such, a stop surface 600 is provided to position the probe tip 602 at the proper registration position.

The stop surface 600 preferably is part of the introducer itself, but it may be formed as a receptacle mounted on the clamp mechanism 218 or as another attached part. In the shown exemplary embodiment, the stop surface 600 comprises an interior surface at the distal tip 208 of the introducer 200. FIG. 6 shows the probe tip 602 spaced slightly from the stop surface 600, but advancing the probe 210 further down will bring the probe tip 602 into contact with the stop surface 600. In this case, contact is via an intermediate cup-like part of a registration indicator 604 (discussed below), but in embodiments that do not have a registration indicator 604 contact may be directly between the probe tip 602 and the stop surface 600. In this embodiment, the offset between the probe tip 602 and the introducer tip 208 can be very small (e.g., <1 mm). In some cases, this small amount of offset may be ignored, but it may nonetheless be included in the computations of the introducer tip location. The stop surface 600 also may be tapered or otherwise shaped to guide the probe tip 602 in to the proper location (e.g., along the central geometric axis of the introducer 200).

It will be appreciated that the stop surface 600 may be configured to contact the probe 210 at a location other than the probe tip 602. For example, the stop surface 600 may comprise a circular ring or arrangement of ribs that surround the probe tip 602 but hold the probe 210 along the tapered surface of the probe 210 immediately above the probe tip 602. In such embodiments, care should be taken to make the support surface 600 strong enough that it will not deform as the probe 210 is pressed downward.

Embodiments also may include a registration indicator to indicate whether the probe 210 is fully inserted into the registration position. While not strictly necessary in all embodiments, a registration indicator can be helpful to ensure that the probe 210 is properly installed into the introducer 200, and that the probe 210 has not slipped during use. It is expected that a registration indicator can be helpful for all systems that combine a probe 210 with an introducer 200, but it may be particularly beneficial in embodiments in which intraoperative removal and reinstallation of the probe 210 is possible or expected.

An example of a registration indicator 604 is shown in FIGS. 2, 6, 7A and 7B. The registration indicator 604 comprises an elongate member 606 that extends from a proximal indicator end 608 located at or near the proximal end 212 of the channel 202, to a distal indicator end 610 located inside the channel 202. The elongate member 606 may comprise a tube, such as shown, to help guide the probe 210 along the length of the elongate member 606, and to prevent the surgeon from inadvertently directing the probe 210 at an improper angle relative to the introducer. The distal indicator end 610 may comprise a closed tip that is tapered towards the center so that the probe 210 will center itself when it is pressed downward into the registration indicator 604 (e.g., to center the probe 210 along the central geometric axis of the introducer 200). If desired, the elongate member 606 may include one or more inspection ports 622 to allow visual inspection inside the elongate member 606 to make sure nothing is blocking free access to the distal indicator end 610. In other embodiments, the elongate member 606 may comprise an open channel that partially wraps around the probe 210, or a simple rod that does not wrap around the probe 210. Also, the closed tip of the distal indicator end 610 may be replaced by a partial or complete ring-like shape that wraps around the probe 210 at a location above the probe tip 602. Other alternatives will be readily apparent to persons of ordinary skill in the art in view of the present disclosure. The registration indicator 604 may be provided as a molded plastic part, as a formed metal part, or by other manufacturing processes.

The elongate member 606 is slideably mounted to the introducer 200, such as by positioning the proximal indicator end 608 inside an upper sliding mount 612 and the distal indicator end 610 inside a lower sliding mount 614. The upper sliding mount 612 in this example comprises a ring joined to the main body 224 of the clamp mechanism 218, either by integral forming or separate manufacture and attachment. The upper sliding mount 612 closely surrounds a similarly-shaped portion of the proximal indicator end 608 to provide sliding movement therebetween along the longitudinal axis 204, while generally preventing relative movement in directions perpendicular to the longitudinal axis 204. Similarly, the lower sliding mount 614 comprises a ring or tube, formed at the distal end 206 of the introducer 200, that surrounds the distal indicator end 610 to provide sliding movement therebetween along the longitudinal axis 204, while generally preventing relative movement in directions perpendicular to the longitudinal axis 204. It will be appreciated that other arrangements of sliding parts or shapes may be used in other embodiments. For example, the ring that forms the upper sliding mount 612 or the lower sliding mount 614 may be replaced by a pattern of ribs or pins that prevent lateral movement away from the longitudinal axis 204. By way of example, FIG. 2 shows the lower sliding mount 614 formed with ribs 236. Other alternatives will be readily apparent to persons of ordinary skill in the art in view of the present disclosure.

A resilient member, such as a spring 616, may be provided to bias the registration indicator 604 away from the tip 208 of the introducer 200. In this example, the spring 616 comprises a coil spring that wraps around the elongate member 606 and extends between a stop ring 618 on the outer surface of the elongate member 606 and an upper surface of the lower sliding mount 614. The stop ring 618 may be provided integrally with the elongate member 606, or added as a separate part. The spring 616 may comprise any suitable material, such as spring steel or resilient plastic. Also, other kinds of springs and spring locations may be used in other embodiments. For example, the coil spring may be replaced by a leaf spring, a cantilevered beam, or an elastomeric material. As another example, the spring may be located between the distal indicator end 610 and the stop surface 600.

The registration indicator 604 may be captured in place by a lip 620, formed on the elongate member 606, that abuts the bottom of the clamp's main body 224, or by other interacting structures. In this example, the registration indicator 604 may be installed by sliding the spring 616 over the distal indicator end 610, placing this subassembly into the introducer 200, then attaching the clamp mechanism 218 to hold the registration indicator 604. With this construction, the entire assembly of the introducer 200, clamp mechanism 218, and registration indicator 604 has no loose parts, which helps provide a high degree of safety in the surgery environment.

In use, the elongate member 606 is movable between a first position in which the proximal indicator end 608 is positioned to indicate that the probe 210 is not in registration with the introducer 200, and a second position in which the proximal indicator end 608 is positioned to indicate that the probe 210 is in registration with the introducer 200. In the registered position, the probe tip 602 may be closely adjacent to the introducer tip 208 (e.g., within about 2.0 mm, 1.0 mm, or less), or the probe tip 602 may be at a larger, but known, position relative to the introducer tip 208. The spring 616 biases the registration indicator towards the first position. When it is desired to install a probe 210, the surgeon inserts the probe tip 602 into the ring-like upper sliding mount 612 and advances the probe tip 602 until it contacts the distal indicator end 610. The surgeon continues advancing the probe tip 602 to compress the spring 616 and slide the registration indicator from the first position to the second position. When the registration indicator 604 indicates that the probe 210 is in proper registration with the introducer 200, the surgeon can engage the clamp mechanism 218 to hold the probe 210 in place.

Figure 7A:
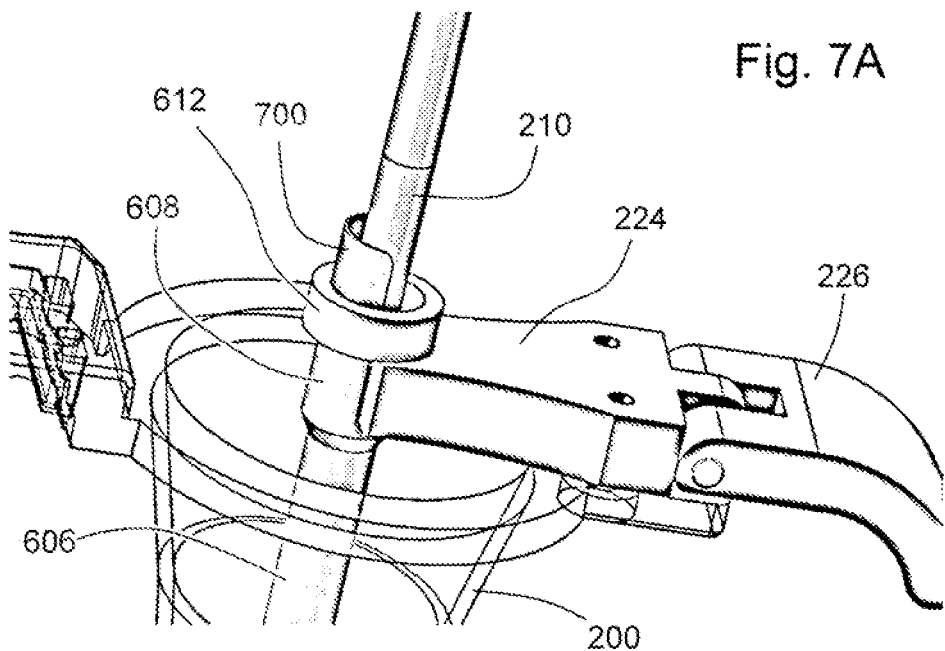
FIGS. 7A and 7B show the registration indicator of FIG. 6 in two positions.
Figure 7B:
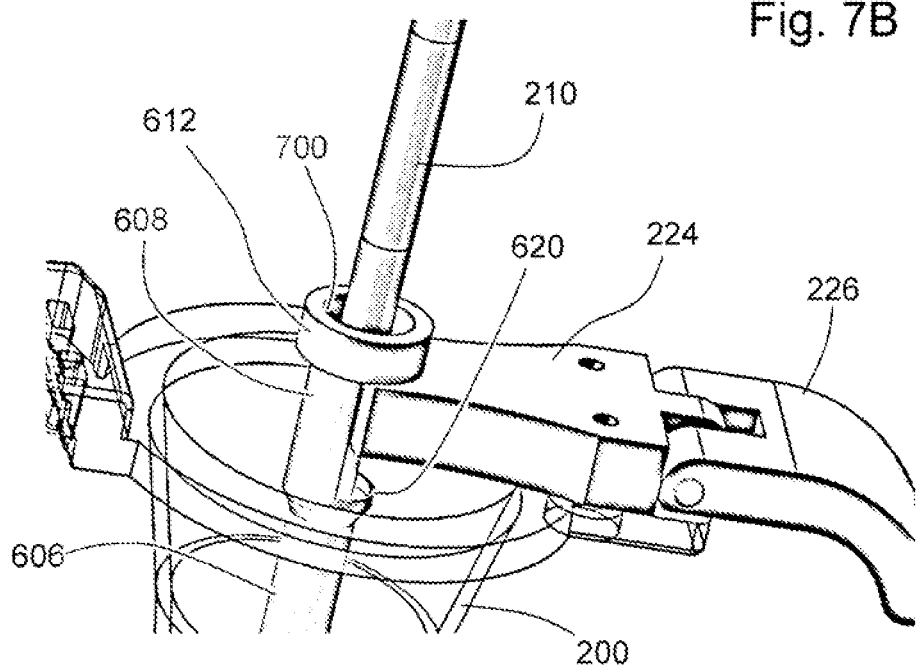

The registration indicator 604 can be configured in any suitable way to indicate improper and proper registration to the surgeon. For example, FIGS. 7A and 7B show the registration indicator 604 in the unregistered and registered positions, respectively. In the unregistered position, an upper indicator surface 700 of the proximal indicator end 608 is positioned above the upper sliding mount 612 to indicate that the probe 210 is not in proper registration. When the probe 210 is fully inserted, the proximal indicator end 608 is moved down to the second position, in which the indicator surface 700 is not visible behind the upper sliding mount 612, to indicate that the probe 210 is now in proper registration with the introducer 200. At this point, the clamp mechanism 218 may be engaged to hold the parts in proper registration. If the probe 210 slips within the clamp mechanism 218 before or during surgery, the spring 616 will move the registration indicator 604 upwards away from the introducer tip 208 to immediately indicate to the surgeon that the probe 210 is no longer in registration.

The indicator surface 700 may be brightly colored (e.g., orange, yellow or red) to help show when it is in the unregistered position. The indicator surface 700 also may include markings such as a textual indication that registration has not been achieved, a scale or ruler to indicate how far the parts are from registration, or other markings. Other alternatives will be readily apparent. For example, the indicator surface 700 may comprise a pointer that remains visible at all times, but points to a word (e.g., "bad") or other indicia (e.g., a red stripe) when the parts are not in registration, and points to another word (e.g., "good") or other indicia (e.g., a green stripe) when the parts are in registration. Other variations will be readily apparent in view of the present disclosure.

The registration indicator 604 also may be protected from inadvertent movement, to prevent it from accidentally being pressed down against the bias of the spring 616 when the probe 210 is not fully seated in the registration position. For example, the registration indicator 604 could be surrounded by a transparent cover or a structure that extends from the upper sliding mount 612. Such structure preferably will not block the surgeon's view of the registration indicator 604.

The shown registration indicator 604 is not operatively connected to the clamp mechanism 218, so that the registration indicator 604 will operate regardless of the clamp's position. In other embodiments, the registration indicator 604 may be interconnected to the clamp mechanism 218, but in such cases the registration indicator 604 may be useful simply to indicate when the clamp mechanism 218 has been disengaged or slipped.

Figure 8:
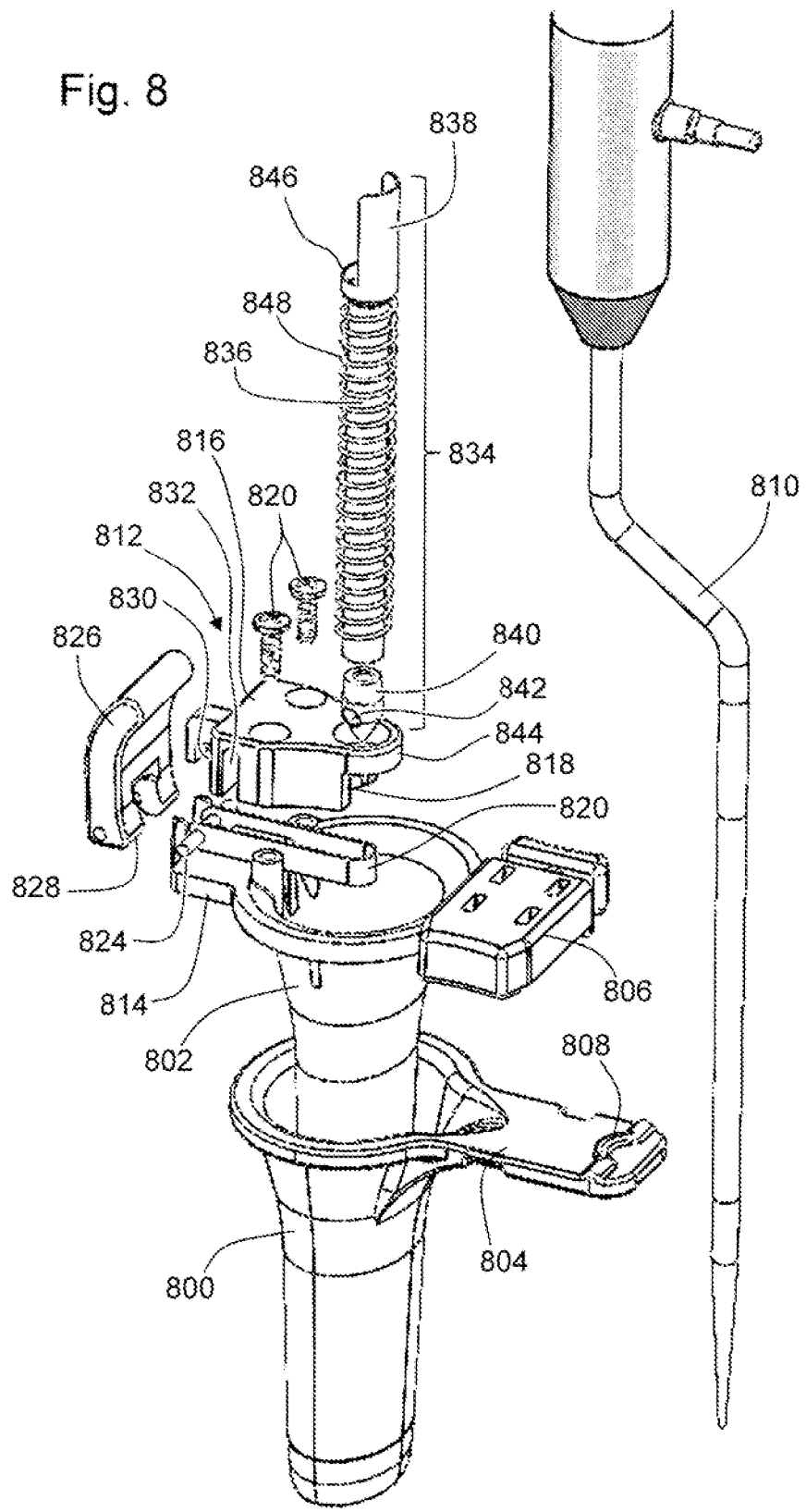
FIG. 8 is an exploded view of another exemplary retractor system, shown with a registration indicator and a navigation probe.

Another exemplary embodiment is illustrated in FIGS. 8, 9A and 9B. Here, the retractor system includes a retractor 800 and an introducer 802 that selectively installs inside the retractor 800. The retractor 800 and introducer 802 have an oval, round, or other cross-sectional shape, and the cross-sectional size of each may gradually decrease towards the distal ends thereof. The retractor 800 and introducer 802 also may be partially or wholly transparent to allow visualization of tissue therethrough. The retractor 804 may include a handle 804, and a lock 806 may be provided on the introducer 802 or retractor 800 to selectively lock the introducer 802 and retractor 800 together. In this case, the lock 806 engages the handle 804, but other arrangements may be used. The handle 804 also may include a ridge 808 or other structure to engage a conventional surgical clamp (not shown).

The introducer 802 includes a clamp mechanism 812 that is configured to selectively hold a navigation probe 810. The clamp mechanism 812 includes a clamp mount 814 that extends from (and may be integrally formed with) the proximal end of the introducer 802, a clamp body 816 and associated anvil 818 that is secured to the clamp mount 814 by screws 820 or the like, a tension band 822, a pivot pin 824 and a clamp lever 826. The clamp mechanism 812 is similar to those described previously herein, but the clamp lever 826 includes one or more protrusions 828 that hold the clamp lever 826 in the locked position, and cooperates with the clamp body 816 to generate a force to hold the tension band 822 against the anvil 818.

The operation of the clamp lever 826 is shown in FIGS. 9A and 9B, which show the clamp mechanism 812 in the unlocked and locked positions, respectively. The clamp lever 826 is pivotally mounted on the pivot pin 824, such as described previously herein, with the protrusion 828 facing an abutment surface 830 on the clamp body 816. As shown in FIG. 9A, the clamp lever 826 starts in a first angular position relative to the rest of the clamp mechanism 812. In this position, the protrusion 828 is positioned to allow the pivot pin 824 to be positioned a first distance $d_1$ from the abutment surface 830. When the clamp lever 826 is rotated about the pivot pin 824 to the locked position, as shown in FIG. 9B, the protrusion 828 presses against the abutment surface 830 to force the pivot pin 824 to a second distance $d^2$ from the clamp body 816. The second distance $d^2$ is greater than the first distance $d_1$, and thus the pivot pin 824 pulls the tension band 820 towards the anvil 818 to clamp the probe 810 in place.

It will be appreciated from the foregoing explanation that the protrusion 828 acts as a rotating cam to selectively clamp or unclamp the probe 810. In the unclamped position, the pivot pin 824 may not necessarily move back to the first distance $d_1$, but it is free to do so upon application of a nominal force, which allows installation of the probe 810 between the tension band 820 and the anvil 818. Alternatively, a return spring (not shown) or other resilient device may be used to move the pivot pin 824 to the first position $d_1$, which may be helpful to allow easier installation of the probe 810.

As noted above, the protrusion 828 is configured to hold the clamp lever 826 in the locked position. This is achieved by configuring the protrusion 828 as a so-called "over-center" mechanism that requires an application of force to move the clamp lever 826 out of the locked position. In the illustrated example, the protrusion 828 is shaped with a point of maximum distance 900 that is located at a greatest distance from the pivot pin 824. The distance between the pivot pin 824 and the abutment surface 830 is greatest when the point of maximum distance 900 is directly between the pivot pin 824 and the abutment surface 830, and the force generated to push the pivot pin 824 away from the abutment surface 830 is also greatest at this point. The point of maximum distance 900 contacts the abutment surface 830 slightly before the clamp lever 826 reaches the locked position. Thus, when the clamp lever 826 is in the locked position such as shown in FIG. 9B, the second distance $d^2$ is slightly less than the maximum distance that is achieved when the point of maximum distance 900 contacts the abutment surface 830. To remove the clamp lever 826 from the locked position, the user must apply a force to rotate the point of maximum distance 900 past the abutment surface. The magnitude of this force can be modified by altering the shape of the protrusion surface 828 and abutment surface 830, by altering the coefficient of friction between the parts, and by other methods as will be appreciated from the foregoing description. Other embodiments also may use other over-center mechanisms, as known in the art.

The amount of force required to rotate the clamp lever 826 and the magnitude of the clamping force generated to hold the probe 810 in place are a function of the geometric relationships of the parts (e.g., the sizes and shapes of the protrusion 828 and abutment surface 830), and also the resilience of the parts (e.g., the flexibility of the tension band 820). In the shown example, the rotation and retaining force are regulated by resiliently mounting the abutment surface 830 to the remainder of the clamp body 816. For example, a slot 832 may be provided behind the abutment surface 820 to mount the abutment surface 830 in a cantilevered configuration that allows the abutment surface to flex towards the rest of the clamp body 816. As the protrusion 828 is moved against the abutment surface 830 by rotating the clamp lever 826, the abutment surface 830 can move towards the clamp body 816. When the protrusion 828 is in the final locked position as shown in FIG. 9B, the abutment surface 830 preferably is still flexed towards the clamp body 816 to some degree to provide a resilient restoring force that holds the probe 810 in place.

Other mechanisms for providing a resilient force to hold the probe 810 may be used in other embodiments. For example, the tension band 820 may be elastically extended when the pivot pin 824 is moved to the second distance $d^2$. As another example, the anvil 818 may be resiliently mounted. As another example, the clamp lever 826 may have a slot behind the protrusion 828 to allow the protrusion 828 to flex somewhat. Other alternatives will be readily apparent to persons of ordinary skill in the art in view of the present disclosure.

The introducer 802 also may include a registration indicator 834. In this example, the registration indicator comprises a shaft 836 with an indicator surface 838 at the proximal end, and a probe tip receptacle 840 at the distal end. The shaft 836 may comprise a solid-walled tube, which minimizes the possibility that the tip of the probe 810 will be turned to the side and miss the tip receptacle 840. Alternatively the shaft 836 may comprise a rod or a tube with side openings to facilitate viewing of the probe 810 and removal of body fluids and the like that might enter during surgery. The tip receptacle 840 may be formed as part of the shaft 836, or formed separately from and joined to the shaft 836 by any suitable bonding method (e.g., ultrasonic welding, laser welding, adhesives, press-fitment, etc.). For example the shown tip receptacle 840 is a machined metal or molded plastic part that is joined to the shaft 836. The tip receptacle 840 also may include an opening 842 through which the proper seating of the probe tip can be confirmed and fluids can be evacuated.

The registration indicator 834 may be mounted to the introducer 802 by being captured in place between the clamp body 816 and the distal end of the introducer 802. For example, the proximal end of the registration indicator 834 may be slideably mounted in a retaining ring 844 on the clamp body 816, and the distal end of the registration indicator 834 may be slideably mounted in a retaining cup 902 at the distal end of the introducer 802. The retaining cup 902 may be configured to allow the tip receptacle 840 and probe tip to get close to the distal exterior end of the introducer 802, to minimize or eliminate the need to account for the distance between the probe tip and the distal exterior end of the introducer 802 during computer-aided navigation. However, this is not strictly required, and some degree of offset can be readily accounted for in calculating the position of the introducer 802 during surgery. The proximal end of the registration indicator 834 includes a lip 846 that abuts the bottom of the clamp body 816 to prevent the registration indicator 834 from being removed.

A spring 848 is positioned between the retaining cup 902 and the shaft 836 to bias the registration indicator 834 away from the distal end of the introducer 802. In this case, the spring 836 extends all the way from the distal end of the introducer 802 (e.g., the top lip of the retaining cup 902), to the proximal end of the registration indicator 834 where the shaft 826 expands radially to transition to the indicator surface 838. Other alternatives to this spring arrangement will be readily apparent to persons of ordinary skill in the art in view of the present disclosure.

As shown in FIG. 9A, the indicator surface 838 is visible above the retaining ring 844 when the probe 810 is not pressed down against the bias of the spring 848. The probe 810 is fully installed by pressing downward to compress the spring 848, so that the tip of the probe 810 is fully-seated in the tip receptacle 840, and the tip receptacle 840 is fully-seated in the introducer 802, as shown in FIG. 9B. In the fully installed position, the indicator surface 838 is no longer visible above the retaining ring 844, which clearly indicates that the parts in in proper position for use.

The foregoing embodiments are expected to provide several benefits to the surgeon during surgery. For example, the introducer and probe can be secured together easily without requiring excessive manipulation or force applied to either part (which is particularly useful where intraoperative removal, reattachment, or adjustment are desired), and the cam lock design is easy to use and gives reliable feedback to indicate that the clamp is properly engaged. Moreover, the clamp can be operated with a single movement of the clamp control mechanism by simply flipping the clamp lever from one position to the other. Also, the parts are securely connected to provide accurate guidance. Still further, the registration indicator provides immediate feedback if the probe releases or shifts out of the registration position relative to the introducer.

The foregoing embodiments also may provide additional manufacturing and operation benefits. For example, the various parts have been combined or integrated to reduce part count to eliminate the possibility of losing loose parts. Also, the parts may be easily molded without requiring excessive tolerance control or major post-molding machining, and the assembled introducer also is manufacturable with relative ease and low cost. Still further, the clamp and registration indicator, or portions thereof, may be manufactured as separate parts that can be integrated into a variety of differently-sized or differently-shaped introducers. Thus, an entire product line of different introducers may be equipped with a single type of clamp or registration indicator with relative ease.

It will be appreciated that the clamp mechanisms described in the foregoing exemplary embodiments may be modified in a variety of ways to provide a surgical introducer that connects to a navigation probe. For example, the pin and tension band may be fixed to the clamp body, and a cam surface on the lever may slide the anvil towards and away from the tension band. In another embodiment, the cam surface may be made separately and mounted to the clamp lever or operated remotely by the cam lever through a linkage. As yet another example, the clamping mechanism may be replaced by a "clothespin" style clamp having a fixed jaw and a pivotally-connected movable jaw. The clamp also may comprise two hooks that move in opposite directions relative to one another (either by both moving or one being fixed and the other moving) to pull on opposite sides of the probe to hold it in place. As another example, the clamp lever may rotate about an axis that is parallel to or at other angles to the longitudinal axis 204. In still other embodiments, the clamp lever 226 may be provided with a double-acting spring, such as used commonly in electrical switches and the like, that urges the clamp towards the open and closed positions. The clamp also may comprise a slot that holds the probe, and a mechanism to selectively squeeze the slot to compress the probe in place. The cam mechanism also may be modified, such as by replacing the simple facing cam surfaces with a spiral-shape slot formed in a rotating disc that drives a pin to clamp the probe in place. The clamp also may comprise a ratchet mechanism to pull the clamp shut on the probe through repeated movements of the ratchet. Other clamps may use a moving wedge or an eccentric pin to drive the clamp closed on the probe. Other alternatives will be readily apparent to persons of ordinary skill in the art in view of the present disclosure, and additional exemplary constructions are described in the priority documents for the present application, which are incorporated herein by reference.

Figure 10:
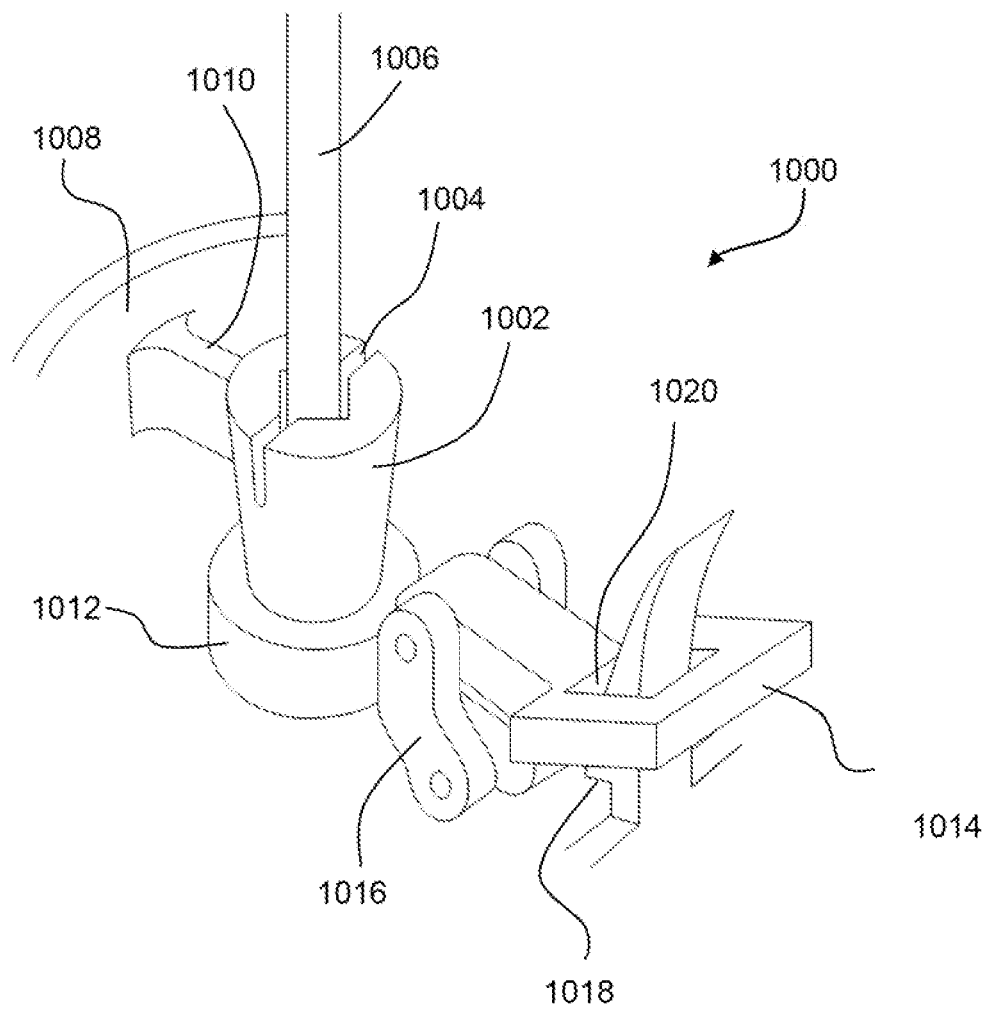
FIG. 10 is another embodiment of an introducer, clamp and navigation probe system.

FIG. 10 shows another clamp 1000. In this embodiment, the clamp 1000 uses a collet that includes a tapered tube 1002 that has a slot 1004 at one end, and a passage through which the probe 1006 fits. The tube 1002 may be connected to the inner wall of the introducer 1008 by a post 1010. The probe 1006 is locked in place by compressing the tube 1002 at the location of the slot 1004. In this example, a collar 1012 is provided to slide up the tube 1002. As the collar 1012 moves upwards, the fixed inner diameter of the collar 1012 encounters the tapered outer body of the tube 1002, and generates a force to compress the tube 1002 against the probe 1006 at the location of the slot 1004. The collar 1012 may be operated by any suitable mechanism, such as a cam lever 1014 that is connected to the collar 1012 by a linkage 1016. The linkage 1016 may comprise any suitable force-transferring mechanism, as known in the art, and preferably provides the collar 1012 with a relatively linear movement. A latch 1018 may be provided to engage an opening 1020 through the cam lever 1014 (or any other part of the cam lever 1014 or linkage 1016), to hold the cam lever 1014 in the locked position until released by the surgeon.

Other alternatives to the disclosed clamps will be readily apparent to persons of ordinary skill in the art in view of the present disclosure. As one non-limiting example, a threaded fastener may be used to secure the probe to the introducer in the fashion of a conventional "locking screw." However, adding a threaded fastener disadvantageously increases the number of articles present at the surgery site, and requires special attention to prevent the threaded fastener from coming free from the introducer and possibly entering the patient's body, or modification to prevent the fastener from coming free at all. Threaded fasteners also may be vulnerable to contamination that can make operation more difficult, require relatively precise machining, can lack a positive engagement feel, can damage the probe, and do not clearly indicate whether they are engaged or not. Moreover, threaded fasteners can be difficult to turn with gloved fingers and can require two hands to secure. Still further, threaded fasteners are not single-action mechanisms, and they cannot be operated with a single movement—instead, the surgeon must repeatedly rotate the screw head to rotate the fastener into position. Such movements tend to move the parts around, and may make it difficult to use the threaded fastener during surgery when maintaining precise positioning of the introducer may be critical. Despite this, a system that uses a threaded fastener may still be used, particularly where setup can be performed remotely from the patient, and such systems are also expected to benefit by the addition of a registration indicator to illustrate when the probe is out of proper registration with the introducer.

The present disclosure also contemplates a variety of modifications to the registration indicator. For example, the spring may abut a structure that extends from the bottom of the main body of the mount, instead of abutting against a part of the introducer. As another example, the registration indicator may comprise a moving part that is captured in a receptacle within the introducer, and is not part of the clamp mounting mechanism. The registration indicator also may comprise any suitable apparatus to indicate the position of the probe, such as a simple protruding pin or a rotating gauge to show the position of the probe more precisely. The registration indicator also may comprise alternative structures, such as a band of material that extends into the introducer and is flexed by the probe to operate a pivoting flag or other indicator when the probe is installed in the introducer. Also, the arrangement of the illustrated upper and lower sliding mounts may be reconfigured to provide other means for holding the registration indicator to slide only along the longitudinal axis. For example, the upper and lower sliding mounts may be replaced by a one or two mounts provided on the clamp body. This latter embodiment is expected to be useful if the introducer has an opening at the tip and it is desired to be able to access that opening while the probe and registration indicator are mounted in place, because the probe tip can be offset from the introducer tip by some distance. Other alternatives will be readily apparent to persons of ordinary skill in the art in view of the present disclosure.

It will be appreciated that the embodiments described herein can be recombined in any suitable manner. For example, the clamps and registration indicators may be connected directly to an introducer, or connected indirectly to an introducer by way of intermediate parts or an adapter that fits inside an introducer. The clamps and registration indicators also may be used directly with retractors. For example, after a retractor as described in a reference such as Mangiardi I is placed at the surgery site, an adapter with a clamp or registration indicator to hold a navigation probe may be placed in or connected to the retractor to confirm that the retractor is in the correct position or to allow further movement of the retractor.

It will also be appreciated that the clamps and registration indicators also may be combined with various different locking mechanisms, position indicators, or other features. Also, parts described in the various embodiments may be recombined with parts from other embodiments in any suitable manner. Still further, it will be understood that the clamp and registration indicator are two separate inventions that may be used independently and without the other. For example, a clamp may be provided without a registration indicator if one is not desired (e.g., to provide greater visibility through the introducer), and a registration indicator may be used without a clamp (e.g., where the surgeon wishes to manually hold the probe in place during use). Other alternatives will be readily apparent to persons of ordinary skill in the art in view of the present disclosure.

Terms of direction or frames of reference are also not intended to be limiting. For example, the term "vertical" and directions that relate to the vertical direction's frame of reference (i.e., "horizontal," "lateral," etc.) have been used herein for expedience to describe embodiments as they would be used with the longitudinal axis 204 of the introducer pointed in the global vertical direction (i.e., along the direction of gravitational pull). It will be appreciated that the introducer can be reoriented to direct the longitudinal axis 204 in directions other than the global vertical direction, and simple rotation of the frame of reference in this manner would not cause commercial embodiments to deviate from the teachings herein.

The present disclosure describes a number of new, useful and nonobvious features and/or combinations of features that may be used alone or together. The embodiments described herein are all exemplary, and are not intended to limit the scope of the inventions. It will be appreciated that the inventions described herein can be modified and adapted in various and equivalent ways, and all such modifications and adaptations are intended to be included in the scope of this disclosure and the appended claims.

We claim:

1. A delicate tissue retraction system for use with a navigation probe having a probe shaft and a probe tip at a distal end of the probe shaft, the delicate tissue retraction system comprising:
   a retractor having a proximal retractor surface and an internal retractor passage extending along a longitudinal axis from the proximal retractor surface to a distal retractor end, wherein the proximal retractor surface extends perpendicular to the longitudinal axis;
   a navigation probe connector configured to be selectively attached to the retractor, the navigation probe connector comprising:
      a central body having an inner passage configured to receive a navigation probe shaft, and an outer wall surrounding the inner passage, and wherein the inner passage extends along the longitudinal axis when the navigation probe connector is attached to the retractor, and
      a connecting body extending radially from the outer wall of the central body and having a lower surface facing towards the proximal retractor surface and extending perpendicular to the longitudinal axis when the navigation probe connector is attached to the retractor, wherein at least a portion of the outer wall of the central body has an outer diameter that is less than an inner diameter of the retractor; and
   an introducer having a proximal introducer end configured to be interposed between the lower surface of the connecting body and the proximal retractor surface when the navigation probe connector is attached to the retractor.

2. The delicate tissue retraction system of claim 1, wherein the navigation probe connector comprises a tapered tip attached to the central body and positioned to extend away from the distal retractor end along the longitudinal axis when the navigation probe connector is attached to the retractor.

3. The delicate tissue retraction system of claim 2, wherein the tapered tip has a maximum outer diameter that is less than a maximum inner diameter of the retractor at the distal retractor end.

4. The delicate tissue retraction system of claim 1, wherein the introducer further comprises a sidewall forming a hollow channel extending from the proximal introducer end to a distal introducer end, wherein the sidewall is configured to extend within the retractor with the distal introducer end protruding from the distal retractor end when the navigation probe connector is attached to the retractor.

5. The delicate tissue retraction system of claim 1, wherein the connecting body is secured to move with the proximal introducer end.

6. The delicate tissue retraction system of claim 5, wherein the connecting body is secured to the proximal introducer end by screws.

7. The delicate tissue retraction system of claim 1, wherein the navigation probe connector further comprises a clamp configured to selectively hold the navigation probe shaft.

8. A delicate tissue retraction system for use with a navigation probe having a probe shaft and a probe tip at a distal end of the probe shaft, the delicate tissue retraction system comprising:
- a retractor having a proximal retractor surface and an internal retractor passage extending along a longitudinal axis from the proximal retractor surface to a distal retractor end, wherein the proximal retractor surface extends perpendicular to the longitudinal axis;
- a navigation probe connector configured to be selectively attached to the retractor, the navigation probe connector comprising:
  - a central body having an inner passage configured to receive a navigation probe shaft, and an outer wall surrounding the inner passage, and wherein the inner passage extends along the longitudinal axis when the navigation probe connector is attached to the retractor,
  - a connecting body extending radially from the outer wall of the central body and having a lower surface facing towards the proximal retractor surface and extending perpendicular to the longitudinal axis when the navigation probe connector is attached to the retractor, and
  - a tapered tip attached to the central body and positioned to extend away from the distal retractor end along the longitudinal axis when the navigation probe connector is attached to the retractor, wherein the tapered tip has a maximum outer diameter that is less than a maximum inner diameter of the retractor at the distal retractor end; and
- an introducer having a proximal introducer end configured to be interposed between the lower surface of the connecting body and the proximal retractor surface when the navigation probe connector is attached to the retractor.

9. The delicate tissue retraction system of claim 8, wherein the introducer further comprises a sidewall forming a hollow channel extending from the proximal introducer end to a distal introducer end, wherein the sidewall is configured to extend within the retractor with the distal introducer end protruding from the distal retractor end when the navigation probe connector is attached to the retractor.

10. The delicate tissue retraction system of claim 8, wherein the connecting body is secured to move with the proximal introducer end.

11. The delicate tissue retraction system of claim 10, wherein the connecting body is secured to the proximal introducer end by screws.

12. The delicate tissue retraction system of claim 8, wherein the navigation probe connector further comprises a clamp configured to selectively hold the navigation probe shaft.

13. A delicate tissue retraction system for use with a navigation probe having a probe shaft and a probe tip at a distal end of the probe shaft, the delicate tissue retraction system comprising:
- a retractor having a proximal retractor surface and an internal retractor passage extending along a longitudinal axis from the proximal retractor surface to a distal retractor end, wherein the proximal retractor surface extends perpendicular to the longitudinal axis; and
- a navigation probe connector configured to be selectively attached to the retractor, the navigation probe connector comprising:
  - a central body having an inner passage configured to receive a navigation probe shaft, and an outer wall surrounding the inner passage, and wherein the inner passage extends along the longitudinal axis when the navigation probe connector is attached to the retractor, and
  - a connecting body extending radially from the outer wall of the central body and having a lower surface facing towards the proximal retractor surface and extending perpendicular to the longitudinal axis when the navigation probe connector is attached to the retractor, wherein at least a portion of the outer wall of the central body has an outer diameter that is less than an inner diameter of the retractor to define a gap between the retractor and the outer wall of the central body, wherein the gap is configured to allow visualization into the internal retractor passage from outside the combined retractor and navigation probe connector.

14. The delicate tissue retraction system of claim 13, further comprising an introducer having a proximal introducer end configured to be interposed between the lower surface of the connecting body and the proximal retractor surface when the navigation probe connector is attached to the retractor.

15. The delicate tissue retraction system of claim 14, wherein the introducer further comprises a sidewall forming a hollow channel extending from the proximal introducer end to a distal introducer end, wherein the sidewall is configured to extend within the retractor with the distal introducer end protruding from the distal retractor end when the navigation probe connector is attached to the retractor.

16. The delicate tissue retraction system of claim 14, wherein the connecting body is secured to move with the proximal introducer end.

17. The delicate tissue retraction system of claim 16, wherein the connecting body is secured to the proximal introducer end by screws.

18. The delicate tissue retraction system of claim 13, wherein the navigation probe connector further comprises a clamp configured to selectively hold the navigation probe shaft.

* * * * *